(12) United States Patent
Mikoshiba et al.

(10) Patent No.: US 6,794,500 B2
(45) Date of Patent: Sep. 21, 2004

(54) RNA-BINDING PROTEIN

(75) Inventors: Katsuhiko Mikoshiba, Tokyo (JP);
Akihiro Mizutani, Tokyo (JP)

(73) Assignee: Riken, Saitama (JP)

( * ) Notice: Subject to any disclaimer, the term of this patent is extended or adjusted under 35 U.S.C. 154(b) by 115 days.

(21) Appl. No.: 09/821,687

(22) Filed: Mar. 30, 2001

(65) Prior Publication Data

US 2002/0106724 A1 Aug. 8, 2002

(30) Foreign Application Priority Data

Sep. 29, 2000 (JP) ........................................ 2000-299812

(51) Int. Cl.⁷ ........................ C07H 21/02; C07H 21/04; C12N 15/00; C12N 15/09; C12N 15/70
(52) U.S. Cl. ................................... 536/23.1; 435/320.1
(58) Field of Search ........................ 536/23.1; 435/320.1

(56) References Cited

PUBLICATIONS

Mizutani et al. SYNCRIP, a cytoplasmic counterpart of herogenous nuclear ribonucleoprotein R, interacts with ubiquitous sunaptotagmin isoforms J. Biol. Chem. vol. 275 Accession No.: AB035725 GenBank Mar. 31, 2000.*

Akihiro Mizutani et al. "SYNCRIP, a Cytoplasmic Counterpart of Heterogeneous Nuclear Ribonucleoprotein R, Interacts with Ubiquitous Synaptotagmin Isoforms.", The Journal of Biological Chemistry, vol. 275, No. 13, pp. 9823–9831, Mar. 31, 2000, Laboratory for Developmental Neurobiology and for Molecular Neurogenesis, the Brain Science Institute, the Institute of Physical and Chemical Research (RIKEN) . . . Japan.

* cited by examiner

Primary Examiner—James Ketter
Assistant Examiner—Konstantina Katcheves
(74) Attorney, Agent, or Firm—Foley & Lardner LLP

(57) ABSTRACT

The present invention provides Synaptotagmin-binding and yet RNA-binding proteins and genes encoding the proteins. The invention relates to a recombinant protein selected from the group consisting of the following (a) and (b), as well as a gene encoding the protein:

(a) a protein comprising the amino acid sequence as shown in SEQ ID NO: 2
(b) a protein which comprises the amino acid sequence as shown in SEQ ID NO: 2 having delection, substitution or addition of one or several amino acids and which has RNA binding activity.

4 Claims, 13 Drawing Sheets

FIG.1
A
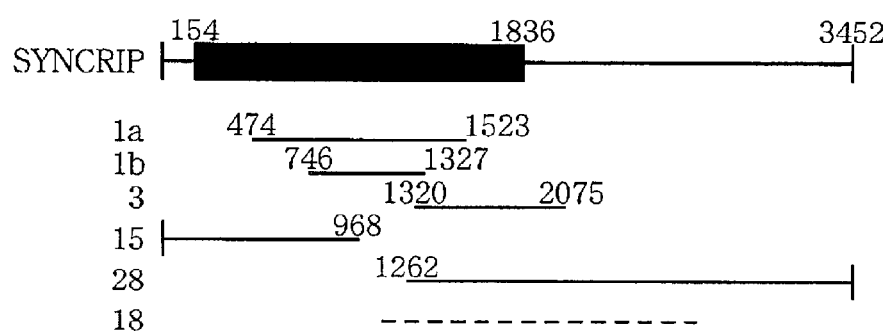
B
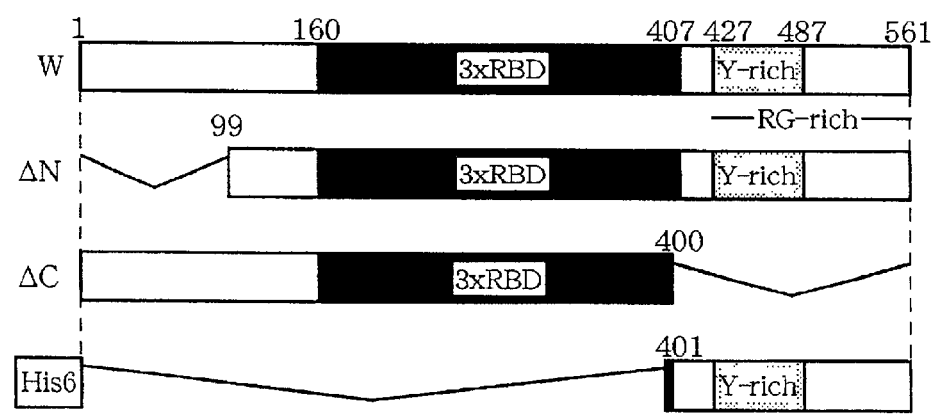

FIG.2

```
SYNCRIP      1:----MATEHVNGNGTEEFMDTTSAVIHSENFQTLLDAGLPQKVAEKLDEIYVAGLVAHSD  56
hnRNPR       1:MANQVNGNAVQLKEEEEPMD-TSSVTHTEHYKTLIEAGLPQKVAERLDEIFQTGLVAYVD  59

SYNCRIP     57:LDERAIEALKEFNEDGALAVLQQFKDSDLSHVQNKSAFLGGVMKTYRDREKQGTKVADSS 116
hnRNPR      60:LDERAIDALREFNEEGALSVLQQFKESDLSHVQNKSAFLCGVMKTYRQREKQGSKVQEST 119

SYNCRIP    117:KGPDEAKIKALLERTGYTLDVTTGQRKYGGPPPDSVYEGQQPSVGTEIYVGKIPRDLFED 176
hnRNPR     120:KGPDEAKIKALLERTGYTLDVTTGQRKYGGPPPDSVYEGVQPGIGTEVFVGKIPRDLYED 179

SYNCRIP    177:ELVPLFEKAGPIWDLRLMHDPLTGLNRGYAFVTFCTKEAAQRAVKLYNNHEIRSGKHIGV 236
hnRNPR     180:ELVPLFEKAGPIWDLRLMHDPLSGQNRGYAFIFFCGKEAAQEAVKLCDSYEIRPGKHLGV 239

SYNCRIP    237:CISVANNRLFVGSIEKSKTKEQILEEFSKVTEGLTDVILYHQPDDKKKNRGFCFLEYEDH 296
hnRNPR     240:CISVANNRLFVGSIPKNKTKENILEEFSKVTEGLVDVILYHQPDDKKKNRGFCFLEYEDH 299
clone-18     1:---------------------------------------------------------DH   2
(m-hnRNPR)

SYNCRIP    297:KTAAQARRRLMSGKVKVWGNVGTVEWADPIEDPDPEVMAKVKVLEVENLANTVTEEILEK 356
hnRNPR     300:KSAAQARRRLMSGKVKVWGNVVTVEWADPVEEPDPEVMAKVKVLFVENLATTVTEEILEK 359
clone-18     3:KSAAQARRRLMSGKVKVWGNVVTVEWADPVEEPDPEVMAKVKVLFVENLATTVTEEILEK  62
(m-hnRNPR)

SYNCRIP    357:SFEQFGKLERVKKLKDYAFIHFDERDGAVKAMEEMNGKDLEGENIEIVFAKPPDQKRKER 416
hnRNPR     360:SFSEFGKLERVKKLKDYAFVHFEDRGAAVKAMDEMNGKEIEGEEIELVLAKPPDKKRKER 419
clone-18    63:SFSEFGKLERVKKLKDYAFVHFEDRGAAVKAMDEMNGKEIEGEEIELVLAKPPDKKRKER 122
(m-hnRNPR)

SYNCRIP    417:KAQRQAARNQMYDDYYYYGPPHMFPPTRGRGR-GGRGGYGYPPDYYGYEDYY-DYYGYDY 474
hnRNPR     420:QAARQASRSTAYEDYYYHPPPRMPPPIRGRGRGGGRGGYGYPPDYYGYEDYYDDYYGYDY 479
clone-18   123:QAARQASRSTAYEDYYYHPPPRMPPPMRGHGR-GGRGGYGYPPDYYGYEDYYDDYYGYDY 181
(m-hnRNPR)

SYNCRIP    475:HNYRGGYEDPYYGYED-FQVGARGRGGRGARGA-AFSHGRGAAPFRGRAGYSQRGGP-GS 531
hnRNPR     480:HDYRGGYEDPYYGYDDGYAVRGRG-GGRGGRGAPPPRGRGAPPPRGRAGYSQRGAPLGP 538
clone-18   182:HDYRGGYEDPYYGYDDGYAVRGRG-GGRGGRGAPPPPRGRGAPPPRGRAGYSQRGAPLGP 240
(m-hnRNPR)

SYNCRIP    532:ARGVRGARGG-AQQQRGRGGKGV-EA-GPDLLQ--------------------------- 561
hnRNPR     539:PRGSRGGRGGPAQQQRGRGSRGSRGNRGGNVGGKRKADGYNQPDSKRRQTNNQQNWGSQP 598
clone-18   241:PRGSRGGRGGPAQQQRGRGSRGARGNRGGNVGGKRKADGYNQPDSKRRQTNNQQNWGSQP 300
(m-hnRNPR)

562:-----------------------------------
hnRNPR     599:IAQQPLQQGGSDYSGNYGYNNDNQEFYQDTYGQQWK                          633
clone-18   301:IAQQPLQQGGDYSGNYGYNNDNQEFYQDTYGQQWK                           335
(m-hnRNPR)
```

FIG.9

RNA-BINDING PROTEIN

BACKGROUND OF THE INVENTION

1. Field of the Invention

The present invention relates to a Synaptotagmin-binding and yet cytoplasmic RNA-binding protein and a gene encoding the protein.

2. Description of the Prior Art

It is known that the release of neurotransmitters from the presynaptic terminal in mammals begins with the fusion of synaptic vesicles with the axon-terminal plasma membrane. The synaptic vesicle protein VAMP1 or 2 and the two presynaptic membrane proteins Syntaxin 1 and SNAP-25 are essential for neurotransmitter release (Scheller, R. H. (1995) Neuron 14, 893–897; Sudhof, T. C. (1995) Nature 375, 645–653; Augustine, G. J. et al. (1996) Annu. Rev. Pharmacol. Toxioccol. 36, 659–701). The formation of a complex among these proteins is the first molecular process for the synaptic vesicle fusion with the above-mentioned plasma membrane.

On the other hand, Synaptotagmin (Syt) is a protein playing an important role in the transport of neurotransmitters and is known to be a family consisting of at least 12 isoforms (Syt-I to Syt-XII) in rat and mouse (Schiavo, G. et al. (1998) Biochem. Biophys. Res. Commun. 248, 1–8; Li, C. et al. (1995) Nature 375, 594–599). Among these isoforms, Syt-I is present on the synaptic vesicle membrane as an integral protein spanning the membrane once. This protein possesses two domains (termed C2A and C2B) homologous to the C2 regulatory region of protein kinase C (Sudhof, T. and Rizo, J. (1996) Neuron 17, 379–388; Schiavo, G. et al., (1998) Biochem. Biophys. Res. Commun. 248, 1–8). Syt-I is one of the proteins involved in neurotransmission and functions via the following mechanism. The C2B domain of Syt-I on synaptic vesicles fuses with the plasma membrane (presynaptic membrane) to thereby open a fusion pore in the synaptic vesicle membrane. Then, neurotransmitters in the synaptic vesicle are transported through the pore.

The present inventor has found that inositol 1,3,4,5-tetrakisphosphate (IP4) binds to the C2B domain of Syt-I, -II, -IV, -VI through -IX and -XI (Fukuda, M. et al. (1994) J. Biol. Chem. 269, 29026–29211; Ibata, K. et al. (1998) J. Biol. Chem. 273, 12267–12273), and demonstrated that inositol high polyphosphate series (IHPS; IP4 and IP6) play an important role in the regulation of Syts-regulated vesicle trafficking (Fukuda, M. and Mikoshiba, K. (1997) BioEssays 19, 593–603). For example, the binding of an inositol high polyphosphate to the C2B domain of Syt inhibits the step of fusion between synaptic vesicles and the presynaptic membrane (Fukuda, M. et al. (1995) Proc. Natl. Acad. Sci. USA 92, 10703–10707; Mochida, S. et al. (1997) Neuroscience 77, 937–943; Ohara-Imaizumi, M. et al. (1997) Proc. Natl. Acad. Sci. USA 92, 10708–10712). Thus, the C2B domain and the presynaptic membrane are separated from each other by the presence of IP4, which results in the inhibition of neurotransmission.

Thus, it is believed that various substances are involved in the interaction of synaptic vesicles with the presynaptic membrane.

OBJECTS AND SUMMARY OF THE INVENTION

It is an object of the invention to provide a Synaptotagmin-binding and yet cytoplasmic RNA-binding protein.

Toward the solution of the above problem, the present inventor has analyzed those proteins capable of binding to Synaptotagmin and succeeded in isolating a protein which binds to Synaptotagmin and yet can bind to cytoplasmic RNA. Thus, the present invention has been achieved.

The present invention relates to the following inventions:

(1) A recombinant protein selected from the group consisting of the following (a) and (b):
  (a) a protein comprising the amino acid sequence as shown in SEQ ID NO: 2
  (b) a protein which comprises the amino acid sequence as shown in SEQ ID NO: 2 having deletion, substitution or addition of one or several amino acids and which has RNA binding activity.

(2) A recombinant protein selected from the group consisting of the following (c) and (d):
  (c) a protein comprising the amino acid sequence as shown in SEQ ID NO: 4
  (d) a protein which comprises the amino acid sequence as shown in SEQ ID NO: 4 having deletion, substitution or addition of one or several amino acids and which has RNA binding activity.

(3) A gene encoding a protein selected from the group consisting of the following (a) and (b):
  (a) a protein comprising the amino acid sequence as shown in SEQ ID NO: 2
  (b) a protein which comprises the amino acid sequence as shown in SEQ ID NO: 2 having deletion, substitution or addition of one or several amino acids and which has RNA binding activity.

(4) A gene encoding a protein selected from the group consisting of the following (c) and (d):
  (c) a protein comprising the amino acid sequence as shown in SEQ ID NO: 4
  (d) a protein which comprises the amino acid sequence as shown in SEQ ID NO: 4 having deletion, substitution or addition of one or several amino acids and which has RNA binding activity.

(5) A gene comprising a DNA selected from the group consisting of the following (e) and (f):
  (e) a DNA comprising the nucleotide sequence as shown in SEQ ID NO: 1
  (f) a DNA which hybridizes to the nucleotide sequence as shown in SEQ ID NO: 1 under stringent conditions and which encodes a protein having RNA binding activity.

(6) A gene consisting of a DNA selected from the group consisting of the following (g) and (h):
  (g) a DNA comprising a nucleotide sequence spanning from position 154 to position 1836 of SEQ ID NO: 3
  (h) a DNA which hybridizes to a DNA comprising a nucleotide sequence spanning from position 154 to position 1836 of SEQ ID NO: 3 and which encodes a protein having RNA binding activity.

(7) A recombinant vector comprising the gene.

(8) A transformant comprising the recombinant vector.

(9) A method of producing an RNA-binding protein comprising culturing the above transformant and recovering the RNA-binding protein from the resultant culture.

(10) An antibody against the protein.

(11) A pharmaceutical composition for regulating neuronal functions, comprising the protein as an active ingredient.

(12) A therapeutic agent for neurological diseases comprising the protein as an active ingredient.

(13) A reagent for detecting a Synaptotagmin-binding and yet RNA-binding protein, comprising an antibody against the protein

(14) A reagent for detecting Synaptotagmin, comprising the protein and/or an antibody against the protein. .

BRIEF DESCRIPTION OF THE DRAWINGS

FIG. 1 shows cDNA clones of various lengths encoding the protein of the invention, SYNCRIP, (panel A) and the construction of truncated SYNCRIP genes (panel B).

FIG. 2 shows an alignment between the amino acid sequence of SYNCRIP (SEQ ID NO: 4) and the amino acid sequences of hnRNP R (SEQ ID NO: 10) and mouse hnRNP R (Clone 18; SEQ ID NO: 11).

FIG. 9 shows the interaction of SYNCRIP with the C2A and/or C2B domain of Syt.

DETAILED DESCRIPTION OF THE INVENTION

Figure 3:
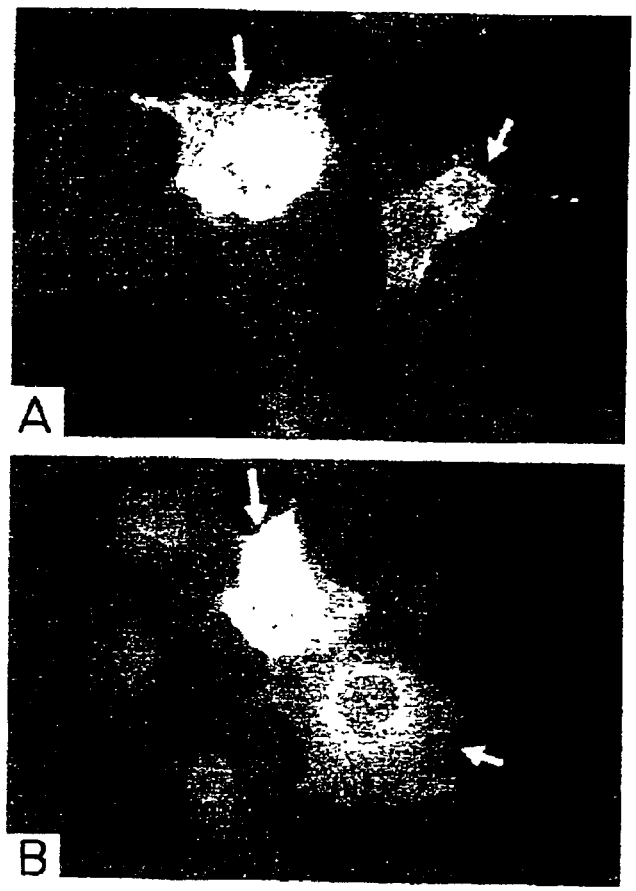
FIG. 3 shows photographs indicating cytoplasmic localization of SYNCRIP.

The protein of the invention is a Synaptotagmin-binding and yet cytoplasmic RNA-binding protein designated SYNCRIP (Synaptotagmin-binding, cytoplasmic RNA-interacting protein)(molecular weight: 66 kDa). One region of SYNCRIP binds to cytoplasmic RNA (in particular, poly(A) region of mRNA) and another region of SYNCRIP binds to the C2B domain of Synaptotagmin on synaptic vesicles. Since synaptic vesicles are transported to the presynaptic terminal after their production in the neurosome, SYNCRIP functions as a "vehicle" for RNA.

As described above, the binding of an inositol high polyphosphate to the C2B domain of Syt inhibits the fusion step of synaptic vesicles with the presynaptic membrane. With respect to this inhibition, the present inventor has analyzed those molecules which interact directly with the C2A and C2B domains of Syt. As a result, a protein which binds to Synaptotagmin and yet binds to cytoplasmic RNA has been found.

1. Isolation of Genes Encoding SYNCRIP (1) Preparation and Screening of cDNA Library The gene of the invention can be isolated by screening a cDNA library prepared from mRNA extracted from mouse or rat cerebellum using a DNA probe synthesized based on a partial amino acid sequence of SYNCRIP purified from cerebellum.

The preparation of mRNA may be performed by conventional techniques. For example, cerebellum tissues or cells are treated with a guanidine reagent or phenol reagent to obtain total RNA. Then, poly($A^+$) RNA (mRNA) is obtained therefrom by the affinity column method using oligo(dT)-cellulose or poly U-Sepharose using Sepharose 2B as a carrier, or by the batch method. Alternatively, poly($A^+$) RNA fraction may be obtained by sucrose density-gradient centrifugation.

With the resultant mRNA as a template, a single-stranded cDNA is synthesized using oligo(dT) primers and a reverse transcriptase. Then, a double-stranded cDNA is synthesized from the single-stranded cDNA. The thus obtained double-stranded cDNA is integrated into an appropriate cloning vector to prepare a recombinant vector. A host such as *E. coli* is transformed with the recombinant vector. The resultant transformants are selected using tetracycline resistance and ampicillin resistance as indicators to thereby obtain a cDNA library.

The transformation of *E. coli* may be performed by conventional techniques. For example, the method of Hanahan (Hanahan, D. (1983) J. Mol. Biol. 166, 557–580) in which a recombinant vector is added to competent cells prepared with calcium chloride, magnesium chloride or rubidium chloride may be used. When a plasmid is used as a vector, the plasmid should contain drug resistance genes against tetracycline, ampicillin, etc. Alternatively, cloning vectors other than plasmid (such as λ phage) may be used.

As a screening method to select those clones having a DNA of interest from the resultant transformants, a method may be used in which a pair of primers are synthesized based on a partial amino acid sequence of SYNCRIP purified from mouse cerebellum, and then a polymerase chain reaction (PCR) is performed using the primers. The purification of SYNCRIP from mouse cerebellum may be performed by suspending the cerebellum in an appropriate buffer, removing cell debris by centrifugation, incubating the homogenate with GST-Syt-II C2AB protein, eluting the bound proteins, separating the proteins by ion exchange chromatography and subjecting the resultant 66 kDa protein-rich fractions to SDS-PAGE.

As a template DNA to be used in the above PCR, a cDNA synthesized from the mRNA by reverse transcription may be given. The primers may be designed based on amino acid sequence information on the purified SYNCRIP, taking into consideration of the expected size of the DNA fragment to be amplified and combinations of regenerate codons. For example, the sense primer may be 5'-GTNACNGA(AG)GGN(TC)TNAC-3' (SEQ ID NO: 8) based on a partial sequence VTEGLT (SEQ ID NO: 6); and the anti-sense primer may be 5'-(TC)TT(AG)TC(AG)TCNGG(TC)TG(AG)TG(AG)TA-3' (SEQ ID NO: 9) based on a partial sequence YHQPDDK (SEQ ID NO: 7). It should be noted that primers which may be used in the PCR are not limited to these primers.

The thus amplified DNA fragment is labeled with such as $^{32}P$, $^{35}S$ or biotin, and hybridized as a probe with a nitrocellulose filter on which the DNA from the transformant has been denatured and immobilized. Thus, positive clones are obtained.

(2) Determination of Nucleotide Sequences

The nucleotide sequences of the thus obtained clones are determined. This sequencing may be performed by conventional techniques such as the chemical modification method of Maxam-Gilbert or the dideoxynucleotide chain termination method using M13 phage. However, sequencing is usually performed with an automated DNA sequencer (e.g., Perkin Elmer model 373A DNA Sequencer; BcaBEST Dideoxy Sequencing Kit (TAKARA)).

The nucleotide sequence of the gene of the invention (full-length cDNA) is shown in SEQ ID NO: 3, and the amino acid sequence of the protein of the invention in SEQ ID NO: 4. In the nucleotide sequence of SEQ ID NO: 3, an open reading frame is formed by a nucleotide sequence from position 154 to position 1836, which encodes the amino acid sequence of SEQ ID NO: 4. Therefore, in addition to the gene consisting of the nucleotide sequence of SEQ ID NO: 3, a gene consisting of the above mentioned nucleotide sequence of the open reading frame region is also included in the gene of the invention.

It should be note that as long as a protein consisting of the amino acid sequence as shown in SEQ ID NO: 4 has RNA binding activity, in particular, activity to bind to the poly(A) sequence of mRNA, the amino acid sequence may have mutations such as deletion, substitution or addition of one or more of amino acids. For example, one or several, preferably about one to ten, more preferably one to five amino acids in the amino acid sequence as shown in SEQ ID NO: 4 may be deleted; one or several, preferably about one to ten, more preferably one to five amino acids may be added to the amino acid sequence as shown in SEQ ID NO: 4; or may be deleted; one or several, preferably about one to ten, more preferably one to five amino acids in the amino acid sequence as shown in SEQ ID NO: 4 may be replaced with other amino acids.

In the present invention, the term "RNA binding activity" means an activity of a region of SYNCRIP to bind to cytoplasmic RNA (in particular, the poly(A) region of mRNA).

Truncated versions of the protein having the amino acid sequence of SEQ ID NO: 4 are also included in the protein of the invention, as long as they have Synaptotagmin binding activity described above. Since a truncated SYNCRIP lacking amino acids 401–561 in SEQ ID NO: 4 (C-terminal truncated version) loses Synaptotagmin binding activity, it can be said that the region of amino acids 401–561 possesses the Synaptotagmin binding activity and that the region of amino acids 1–400 does not have any effect on the Synaptotagmin binding activity of SYNCRIP. Therefore, a protein having the amino acid sequence of the above-mentioned positions 401–561 (SEQ ID NO: 2) (i.e., the amino acid sequence of SEQ ID NO: 4 lacking amino acids 1–400) is also included in the protein of the invention, for example. Furthermore, a protein comprising the amino acid sequence as shown in SEQ ID NO: 4 may have mutations, such as deletion, substitution or addition of one to several, preferably one to ten, and more preferably one to five amino acids within the region which does not have any effect on the Synaptotagmin binding activity (i.e., the region of amino acids 1–400 in SEQ ID NO: 4). Further, the above-described truncated proteins which have mutation(s) in one or several amino acids are also included in the protein of the invention, as long as they have Synaptotagmin binding activity.

Accordingly, genes encoding proteins having the above-described mutation-introduced amino acid sequences, or genes encoding truncated SYNCRIP proteins or mutated versions thereof are also included in the gene of the invention as long as the proteins encoded by them have Synaptotagmin binding activity.

The protein of the invention, SYNCRIP, is a protein which can also binds to Synaptotagmin. As long as the protein of the invention has the ability to bind to Synaptotagmin, the target of binding may be any of the isoforms of Syt-I to -XI. Preferably, the protein of the invention binds to Syt-I and -II.

Furthermore, a DNA which can hybridize to the above-described gene of the invention under stringent conditions is also included in the gene of the invention. The term "stringent conditions" means, for example, sodium concentrations of 600–900 mM and temperatures of 60–68° C., preferably 65° C.

The introduction of a mutation into a gene may be performed by known techniques such as the method of Kunkel or the gapped duplex method, or by techniques based on these methods. For example, a mutation may be introduced with a commercial mutagenesis kit using the site-specific mutagenesis technique (e.g., Mutant-K or Mutant-G; Takara) or LA PCR in vitro Mutagenesis Series kit (Takara).

Once the nucleotide sequence of the gene of the invention has been determined, the gene of the invention can be obtained by chemical synthesis, by PCR using the cDNA of the gene as a template, or by hybridizing a DNA fragment having the nucleotide sequence of the gene as a probe.

2. Preparation of Recombinant Vectors and Transformants (1) Preparation of Recombinant Vectors The recombinant vector of the invention can be obtained by ligating (inserting) the gene of the invention into an appropriate vector. The vector into which the gene of the invention is to be inserted is not particularly limited as long as it is replicable in a host. For example, plasmid DNA, phage DNA or the like may be used.

Specific examples of plasmid DNA which may be used in the invention include *E. coli*-derived plasmids (e.g., pREST, pBR322, pBR325, pUC118, pUC119, pUC18 and pUC19), *Bacillus subtilis*-derived plasmids (e.g., pUB110 and pTP5) and yeast-derived plasmids (e.g., YEp13, YEp24 and YCp50). Specific examples of phage DNA which may be used in the invention include λ phages (e.g., Charon4A, Charon21A, EMBL3, EMBL4, λgt10, λgt11 and λZAP). Further, an animal virus vector such as retrovirus or vaccinia virus; or an insect virus vector such as baculovirus may also be used.

For insertion of the gene of the invention into a vector, a method may be employed in which the purified DNA is digested with an appropriate restriction enzyme and then inserted into the restriction site or multi-cloning site of an appropriate vector DNA for ligation.

The gene of the invention must be operably linked to the vector. For this purpose, the vector of the invention may contain, if desired, cis elements such as an enhancer, a splicing signal, a poly(A) addition signal, selection markers, a ribosome binding sequence (SD sequence) or the like in addition to a promoter and the gene of the invention. As the selection marker, dihydrofolate reductase gene, ampicillin resistance gene, neomycin resistance gene, or the like may be enumerated.

(2) Preparation of Transformants

The transformant of the invention may be obtained by introducing the recombinant vector of the invention into a host so that the gene of interest can be expressed. The host is not particularly limited as long as it can express the DNA of the invention. Specific examples of hosts which may be used in the invention include Escherichia bacteria such as *E. coli*; Bacillus bacteria such as *Bacillus subtilis*; Pseudomonas bacteria such as *Pseudomonas putida*; and Rhizobium bacteria such as *Rhizobium meliloti*. Further, yeasts such as *Saccharomyces cerevisiae, Schizosaccharomyces pombe*; animal cells such as COS cells, CHO cells; and insect cells such as Sf9 cells, Sf21 cells may be used.

When a bacterium such as *E. coli* is used as a host, the recombinant vector of the invention is preferably not only capable of autonomous replication in the host but also composed of a promoter, a ribosome binding sequence, the gene of the invention and a transcription termination sequence. The vector may also contain a gene that controls the promoter.

Specific examples of *E. coli* strains which may be used in the invention include *E. coli* K12 and DH1. Specific examples of Bacillus bacteria which may be used in the invention include *Bacillus subtilis* strains. As a promoter, any promoter may be used as long as it can direct the expression of the gene of the invention in a host such as *E. coli*. For example, an *E. coli*- or phage-derived promoter such as trp promoter, lac promoter, $P_L$ promoter or $P_R$ promoter may be used. Alternatively, an artificially altered promoter such as tac promoter may also be used. As a method for introducing the recombinant vector into a bacterium, any method of DNA transfer into bacteria may be used. For example, a method using calcium ions (Cohen, S. N. et al., Proc. Natl. Acad. Sci., USA, 69:2110–2114 (1972)) or electroporation may be used.

When yeast is used as the host, *Saccharomyces cerevisiae*, *Schizosaccharomyces pombe* or *Pichia pastoris* may be used, for example. A promoter which may be used in this case is not particularly limited. Any promoter may be used as long as it can direct the expression of the gene of the invention in yeast. For example, GAL1 promoter, GAL10 promoter, heat shock protein promoter, MFα1 promoter, PH05 promoter, PGK promoter, GAP promoter, ADH promoter, or AOX1 promoter may be enumerated. As a method of introducing the recombinant vector into yeast, any method of DNA transfer into yeast may be used. For example, electroporation (Becker, D. M., Methods Enzymol., 194:182–187 (1990)), the spheroplast method (Hinnen, A. et al., Proc. Natl. Acad. Sci., USA, 75:1929–1933 (1978)), or the lithium acetate method (Itoh, H., J. Bacteriol., 153:163–168 (1983)) may be enumerated.

When an animal cell is used as the host, simian COS-7 or Vero cells, Chinese hamster ovary cells (CHO cells), mouse L cells, rat GH3 cells, human FL cells; or the like may be used. As a promoter, SRα promoter, SV40 promoter, LTR promoter, CMV promoter or the like may be used. The early gene promoter of human cytomegalovirus may also be used. As a method of introducing the recombinant vector into an animal cell, electroporation, the calcium phosphate method, or lipofection may be used, for example.

When an insect cell is used as the host, Sf9 cells, Sf21 cells or the like may be used. As a method for introducing the recombinant vector into an insect cell, the calcium phosphate method, lipofection, or electroporation may be used, for example.

3. Production of SYNCRIP

The protein of the invention can be obtained by culturing the above-described transformant and recovering the protein from the resultant culture. The term "culture" means any of the following materials: culture supernatant, cultured cells or microorganisms, or disrupted products from cultured cells or microorganisms. The cultivation of the transformant of the invention is carried out in accordance with conventional methods commonly used for culturing hosts.

As a medium to culture the transformant obtained from a microorganism host such as *E. coli* or yeast, either a natural or synthetic medium may be used as long as it contains carbon sources, nitrogen sources and inorganic salts assimilable by the microorganism and is capable of effective cultivation of the transformant. As carbon sources, carbohydrates such as glucose, fructose, sucrose, starch; organic acids such as acetic acid, propionic acid; and alcohols such as ethanol and propanol may be used. As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor and the like may be used. As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

Usually, the cultivation is carried out under aerobic conditions (such as shaking culture or aeration agitation culture) at 37° C. for 6 to 24 hrs. During the cultivation, the pH is maintained at 7.0 to 7.5. The pH adjustment is carried out using an inorganic or organic acid, or an alkali solution or the like. During the cultivation, an antibiotic such as ampicillin or tetracycline may be added to the medium if necessary.

When a microorganism transformed with an expression vector containing an inducible promoter is cultured, an inducer may be added to the medium if necessary. For example, when a microorganism transformed with an expression vector containing lac promoter is cultured, isopropyl-β-D-thiogalactopyranoside (IPTG) may be added to the medium. When a microorganism transformed with an expression vector containing trp promoter is cultured, indoleacrylic acid (IAA) may be added to the medium.

As a medium to culture a transformant obtained from an animal cell as a host, commonly used RPMI1640 medium or DMEM medium, or one of these media supplemented with fetal bovine serum, etc. may be used. Usually, the cultivation is carried out in the presence 5% $CO_2$ at 37° C. for 1 to 30 days. During the cultivation, antibiotics such as kanamycin or penicillin may be added to the medium if necessary.

After the cultivation, SYNCRIP protein of the invention is recovered by disrupting the microorganisms or cells, if the protein is produced within the microorganisms or cells. If SYNCRIP protein of the invention is produced outside the microorganisms or cells, the culture fluid is used as it is or subjected to centrifugation to remove the microorganisms or cells. Thereafter, the resultant supernatant is subjected to conventional biochemical techniques used for isolating/purifying proteins. These techniques include ammonium sulfate precipitation, gel chromatography, ion exchange chromatography and affinity chromatography, and may be used independently or in an appropriate combination. Thus, SYNCRIP protein of the invention can be isolated and purified from the above-mentioned culture.

4. Antibodies Against SYNCRIP (1) Preparation of Antigen

In the present invention, antibodies against SYNCRIP may be prepared using the SYNCRIP isolated and purified as described above or a fragment thereof as an antigen.

(2) Preparation of Polyclonal Antibodies Against SYNCRIP of the Invention

Animals are immunized with the antigen prepared as described above. If the animal is rabbit, the dose of the antigen is 100–500 μg/rabbit when an adjuvant is used. Examples of adjuvants useful in the present invention include Freund's complete adjuvant (FCA), Freund's incomplete adjuvant (FIA) and aluminium hydroxide adjuvant.

Immunization is carried out by administering the antigen to a mammal (e.g., rat, mouse or rabbit). The antigen is administered intravenously, subcutaneously or intraperitoneally. The interval of immunization is not particularly limited. immunization is carried out 1 to 10 times, preferably 2 to 3 times, at intervals of several days to several weeks, preferably 2 to 3 weeks. Antibody titer is determined daily from day 6 to day 60 after the final immunization. When the maximum antibody titer is shown, blood is taken from the animal to thereby obtain an anti-serum. The determination of antibody titer may be performed by ELISA (enzyme-linked immunosorbent assay), RIA (radioimmunoassay) or the like.

If purification of an antibody from the anti-serum is needed, purification may be performed by conventional methods such as ammonium sulfate salting out, ion exchange chromatography, gel filtration or affinity chromatography. These methods may be used independently or in combination.

(3) Preparation of Monoclonal Antibodies Against SYN-CRIP of the Invention (3-1) Immunization and Recovery of Antibody-producing Cells Animals are immunized with the antigen prepared as described above. If necessary, an adjuvant (commercial Freund's complete adjuvant, Freund's incomplete adjuvant, etc.) may be mixed with the antigen for efficient immunization.

Immunization is carried out by administering the antigen to a mammal (e.g., rat, mouse or rabbit). If the animal is mouse, the dose of the antigen per administration is 50 $\mu$g/mouse. In principle, the antigen is administered intravenously, subcutaneously or intraperitoneally. The interval of immunization is not particularly limited. Immunization is carried out at least 2 to 3 times at intervals of several days to several weeks, preferably 2 to 3 weeks. After the final immunization, antibdy-producing cells are recovered. Examples of antibody-producing cells include spleen cells, lymph node cells and peripheral blood cells. Among all, spleen cells are preferable.

(3-2) Cell Fusion

In order to obtain hybridomas, antibody-producing cells and myeloma cells are fused. As myeloma cells to be fused with antibody-producing cells, a commonly available cell strain derived from an animal such as mouse may be used. Preferable cell strains are those which have drug selectivity and cannot survive in HAT selection medium (containing hypoxanthine, aminopterin and thymidine) when unfused, but can survive therein only when fused with antibody-producing cells. Specific examples of myeloma cells useful in the present invention include mouse myeloma cell strains P3X63-Ag.8.U1 (P3U1), P3/NSI/1-Ag4-1 and Sp2/0-Ag14.

Cell fusion between the above-described myeloma cells and antibody-producing cells is performed as follows. Briefly, the antibody-producing cells and myeloma cells are mixed at a ratio between 15:1 and 25:1 in an animal cell culture medium such as serum-free DMEM or RPMI-1640. Then, fusion reaction is performed in the presence of a cell fusion promoter such as polyethylene glycol, or by electric pulse treatment (e.g., electroporation).

(3-3) Selection and Cloning of Hybridomas

Hybridomas of interest are selected from fused cells. For example, fused cells are cultured in a medium containing hypoxanthine, aminopterin and thymidine. Then, cells growing therein are obtained as hybridomas.

Subsequently, culture supernatants of grown hybridomas are screened for the presence of antibodies of interest. The screening of hybridomas may be performed by any of the conventional methods. For example, a part of the culture supernatant contained in a well in which a hybridoma is growing may be taken and screened by ELISA, RIA or the like. The cloning of fused cells is performed by, for example, the limiting dilution method. Finally, hybridomas which are monoclonal antibody-producing cells are established.

(3-4) Recovery of Monoclonal Antibodies

The recovery of monoclonal antibodies from the established hybridomas may be performed by conventional cell culturing methods. Briefly, the hybridomas are cultured in an animal cell culture medium (such as 10% fetal bovine serum-containing RPMI-1640 or MEM medium) under conventional culture conditions (e.g., at 37° C., under 5% $CO_2$) for 3 to 10 days. Then, antibodies are recovered from culture supernatants.

In the above-described method for recovering antibodies, the antibodies may be purified, if necessary, by conventional methods such as ammonium sulfate fractionation, ion exchange chromatography, affinity chromatography and gel chromatography. These methods may be used independently or in combination.

5. Pharmaceutical Compositions for Regulating Neuronal Functions

As described above, the protein of the invention can bind to both RNA and Synaptotagmin, and Synaptotagmin moves from the neurosome to the nerve terminal. Therefore, the protein of the invention performs a function of transporting RNA molecules encoding neurotransmitters to the nerve terminal. Accordingly, the gene or the protein of the invention may be used as a regulator for allowing the expression of neurotransmitters at the nerve terminal, i.e., as a pharmaceutical for regulating neuronal functions. The gene or the protein of the invention is useful as an activator for neurons or an agent for gene therapy for neurological diseases.

The therapeutic agent or agent for gene therapy of the invention can be administered orally or parenterally and systemically or locally.

When the protein or the gene of the invention is used as a therapeutic agent or an agent for gene therapy for neurological diseases, the target of use is not particularly limited. For example, the agent of the invention may be used for a specific purpose of treating or preventing neurological diseases such as Parkinson's disease and Alzheimer's disease which develop when neurotransmission does not function or is decreased. Such a disease may be an independent disease, or may be complicated with other neurological disease, or may be complicated with even a disease other than neurological diseases; in any case, such a disease may be the target of use of the protein or gene of the invention.

When the regulator of the invention is administered orally, the regulator may be prepared into any of the formulations such as tablets, capsules, granules, powder, pills, troches, internal liquid agents, suspensions, emulsions or syrups. Alternatively, the regulator may be prepared into a dry product which is re-dissolved just before use. When the regulator of the invention is administered parenterally, the regulator may be formulated into intravenous injections (including drops), intramuscular injections, intraperitoneal injections, subcutaneous injections, suppositories, or the like. Injections are supplied in the form of unit dosage ampules or multi-dosage containers.

These formulations may be prepared by conventional methods using appropriate excipients, fillers, binders, wetting agents, disintegrating agents, lubricating agents, surfactants, dispersants, buffers, preservatives, dissolution aids, antiseptics, flavoring/perfuming agents, analgesics, stabilizers, isotonic agents, etc. conventionally used in pharmaceutical preparations.

Each of the above-described formulations may contain pharmaceutically acceptable carriers or additives. Specific examples of such carriers or additives include water, pharmaceutically acceptable organic solvents, collagen, polyvinyl alcohol, polyvinyl pyrrolidone, carboxyvinyl polymers, sodium alginate, water-soluble dextran, sodium carboxymethyl starch, pectin, xanthan gum, gum arabic, casein, gelatin, agar, glycerol, propylene glycol, polyethylene glycol, vaseline, paraffin, stearyl alcohol, stearic acid, human serum albumin, mannitol, sorbitol and lactose. One or a plurality of these additives are selected or combined appropriately depending of the form of the preparation.

The dosage levels of the therapeutic agent of the invention will vary depending on such factors as the age of the subject, the route of administration and the number of times of administration, and may be varied in a wide range. When an effective amount of the protein of the invention is administered in combination with an appropriate diluent and a pharmaceutically acceptable carrier, the effective amount of the protein may be in the range from 0.01 to 1000 mg/kg body weight per administration. The therapeutic agent may be administered once a day or in several dosages per day.

When the gene of the invention is used as an agent for gene therapy to treat neurological diseases, the gene of the invention may be directly administered by injection, or a vector incorporating the gene of the invention may be administered. Specific examples of a suitable vector for this purpose include an adenovirus vector, adeno-associated virus vector, herpes virus vector, vaccinia virus vector and retrovirus vector. By using such a virus vector, the gene of the invention can be administered efficiently. Alternatively, the gene of the invention may be enclosed in phospholipid vesicles such as liposomes, and the resultant liposomes may be administered to the subject. Since liposomes are closed vesicles containing a biodegradable material, the gene of the invention and liposomes are mixed so that the gene is retained in the internal aqueous layer and lipid bilayer of the liposomes (a liposome-gene complex is formed). Subsequently, when this complex is cultured with cells, the gene in the complex is taken into the cells (lipofection). Then, the resultant cells may be administered by the methods as described below.

As a method of administration of the agent for gene therapy of the invention, local administration to the central nervous system (such as the brain, spiral cord) may be performed in addition to conventional systemic administration such as intravenous or intra-arterial administration. Further, an administration method combined with catheter techniques or surgical operations may also be employed.

The dosage levels of the agent for gene therapy of the invention vary depending on such factors as the age, sex and conditions of the subject, the route of administration, the number of times of administration, and the type of the formulation. Usually, it is appropriate to administer the gene of the invention in an amount of 0.1–100 mg/adult body per day.

6. Reagents for Detecting SYNCRIP

Since the antibody of the invention reacts with SYNCRIP or a fragment thereof, the antibody may be used as a reagent for detecting SYNCRIP. The method of detection of SYNCRIP is not particularly limited. For example, Western blotting may be employed. A test sample (e.g., cell component or subcellular fraction) is fractionated by such as electrophoresis and then reacted with the antibody of the invention which has been labeled (e.g., radioactively or fluorescently) in advance, followed by detection of signals.

The antibody used for the detection of SYNCRIP may be either an antibody against a protein having the full-length amino acid sequence of SYNCRIP or an antibody against a peptide having a partial amino acid sequence of SYNCRIP.

7. Reagents for Detecting Synaptotagmin

Since SYNCRIP of the invention or a fragment thereof (e.g., truncated SYNCRIP) can bind to Synaptotagmin, the protein or the fragment thereof may be used as a reagent for detecting Synaptotagmin. Synaptotagmin contains C2A and C2B domains, and SYNCRIP binds to the C2B domain. Thus, in the present invention, the C2B domain of Synaptotagmin can be the target of detection.

The detection of Synaptotagmin may be performed by reacting a test sample (cell lysate) with SYNCRIP or a fragment thereof and subjecting the reaction product to Western blotting. For example, a cell lysate or subcellular fraction containing Synaptotagmin is fractionated by electrophoresis and then reacted with SYNCRIP or a fragment thereof pre-labeled radioactively or fluorescently, followed by detection of signals. Alternatively, a fusion protein between Synaptotagmin and GST (glutathione-S-transferase) is prepared by conventional methods and then reacted with SYNCRIP. The reaction product is recovered with glutathione-Sepharose and subjected to Western blotting to detect signals.

In the above Western blotting, a labeled antibody against SYNCRIP or a fragment thereof is used to determine signals generated by the antibody. Thus, the antibody may also be used as a reagent for detecting Synaptotagmin.

PREFERRED EMBODIMENTS OF THE INVENTION

Hereinbelow, the present invention will be described more specifically with reference to the following Examples. However, the technical scope of the present invention is not limited to these Examples.

EXAMPLE 1

Isolation of SYNCRIP and Cloning of SYNCRIP Gene (1) Determination of Partial Amino Acid Sequences of SYNCRIP from Mouse Brain SYNCRIP was partially purified as previously described (Mizutani, A. et al. (1997) Biochem Biophys. Res. Commun. 240, 128–131) with some improvement.

Briefly, whole brains (50 g in wet weight) from 8-week old DDY mice were homogenized in 250 ml of a solution containing the following components using a glass-Teflon homogenizer (930 rpm, 10 strokes):

10 mM HEPES-NaOH (pH 7.4)

140 mM NaCl 2 mM EDTA 1 mM β-Mercaptoethanol 0.2 mM Phenylmethylsulfonyl fluoride (PMSF)

10 $\mu$M Pepstatin A

After removal of cell debris and nuclear crude fractions by low-speed centrifugation (1,000×g, 10 min), Triton X-100 was added to give a supernatant fraction (S1) with a final concentration of 1% (w/v). This fraction (S1) was left on ice for 30 min, and then ultracentrifuged at 16,000×g for 30 min to obtain a soluble fraction, which was incubated with purified GST-Syt-II C2AB protein (5 mg) at 4° C. for 4 hr. To the resultant mixture, 1 ml (50% slurry) of glutathione-Sepharose was added and incubated at 4° C. for 1 hr. After extensive washing with a wash buffer (10 mM HEPES-NaOH (pH 7.4), 140 mM NaCl, 2 mM EDTA and 1 mM β-mercaptoethanol), the bound proteins were eluted with 100 $\mu$M IP6 in the wash buffer. The eluted proteins were separated further by MonoA ion exchange chromatography.

As a result, a 66 kDa protein was eluted at around 0.2 M NaCl, pH 8.0. Fractions rich in the 66 kDa protein were subjected to 10% SDS-polyacrylamide gel electrophoresis followed by staining with Coomassie Brilliant Blue R. The 66 kDa protein band was cut out from the gel and digested with lysylendopeptidase (Wako Purechemical) as described previously (Rosenfeld, J. et al. (1992) Annal. Biochem. 203, 173–179). The resultant polypeptides were separated with a C-18 reversed-phase column (MRPC C2/C18 SC 2.1/10; Amersham Pharmacia Biotech) connected to SMART system (Amersham Pharmacia Biotech). Peptide sequences for individual peptides were determined with Perkin Elmer Biosystems 492 protein sequencer.

(2) Cloning of a cDNA Encoding the 66 kDa Protein SYNCRIP

A pair of degenerate primers corresponding to partially digested peptide 1 (VTEGLTDVILYHQPDDK; SEQ ID NO: 5) were synthesized. Sense primer was based on the sequence VTEGLT (SEQ ID NO: 6), and anti-sense primer was based on the sequence YHQPDDK (SEQ ID NO: 7).

Sense primer: 5'-GTNACNGA(AG)GGN(TC)TNAC-3' (SEQ ID NO: 8)

Anti-sense primer: 5'-(TC)TT(AG)TC(AG)TCNGG(TC)TG(AG)TG(AG)TA-3' (SEQ ID NO: 9)

With these primers, PCR was performed for 35 cycles (at 94° C. for 30 sec, at 55° C. for 1 min and at 72° C. for 1 min) using a random-primed, mouse cerebellum-derived first strand cDNA as a template and a Takara PCR kit. The resultant 51 bp PCR product was cloned into pT7Blue (Novagen) followed by confirmation of the sequence thereof.

This 51 bp fragment was labeled with [α-$^{32}$P] dCTP (Amersham Pharmacia Biotech) and used as a probe for screening about $5.0 \times 10^5$ plaques from a mouse cerebellum-derived cDNA library.

Partial amino acid sequences of the 66 kDa protein were determined as described above, and cDNAs were isolated based on the amino acid sequences determined. As a result, several clones partially overlapping were obtained (FIG. 1A). Using a 5'- or 3'-end fragment (about 200 bp) of clone 1a (FIG. 1) as a hybridization probe, a λgt cDNA library was screened to thereby obtain a cDNA encoding the full-length SYNCRIP. The cloned EDNA was subcloned into pBluescript and sequenced in both directions by the dideoxy chain termination method (BcaBEST Dideoxy Sequencing Kit; Takara).

The nucleotide sequence of the gene (cDNA) encoding the full-length SYNCRIP is shown in SEQ ID NO: 3. The amino acid sequence of SYNCRIP (open reading frame) is shown in SEQ ID NO: 4.

The homology analysis of the deduced amino acid sequence of the cloned cDNA revealed that this amino acid sequence is highly homologous to human heterogeneous nuclear ribonucleoprotein R (hnRNP R) (FIG. 2). hnRNP R is a 82 kDa protein defined by Hassefeld et al. (Hassefeld, W. et al. (1998) Nucleic Acids Res. 26, 439–445). This protein is known to be localized in the nucleoplasm and, as described later, is completely different from SYNCRIP of the invention in terms of function.

EXAMPLE 2

Expression of SYNCRIP (1) Localization of SYNCRIP

In this Example, both SYNCRIP and hnRNP R were expressed in COS-7 cells and their behaviors were examined in order to confirm the region of expression of SYNCRIP within cells as well as to demonstrate that SYNCRIP and hnRNP R are functionally different substances. The procedures were as described below.

For transient expression of SYNCRIP in COS-7 cells, an EcoRI site and an XhoI site were introduced by PCR to the 5'- and 3'-ends of the full-length SYNCRIP cDNA, respectively. The resultant DNA fragment was subcloned into plasmid pCDNA3 (Invitrogen). This gene construct was transfected into COS-7 cells with Lipofectamine reagent (Life Technologies) according to the manufacturer's instructions.

On the other hand, two types of polyclonal antibodies against SYNCRIP were prepared for the purpose of Western blotting. One is against an N-terminal region of SYNCRIP (the boxed region in FIG. 2) and designated anti-SYNCRIP-N antibody. The other is against a region with complete homology between SYNCRIP and hnRNP R (the double underlined region in FIG. 2) and designated anti-SYNCRIP-Pep antibody.

These antibodies were prepared as described below.

(i) Anti-SYNCRIP-N Antibody

A $(His)_6$-tagged recombinant protein comprising the N-terminal region of SYNCRIP (amino acids 1–170) was expressed in E. coli and partially purified with ProBond resin (Invitrogen). Then, the protein was fully purified by MonoQ column chromatography. Three hundred micrograms of the purified protein was administered to Japan White rabbits together with Freund's complete adjuvant for immunization (subcutaneous injection, at intervals of 14 days). On the other hand, a GST fusion protein containing a region corresponding to the above antigenic protein was covalently bound to a carrier and packed in a column to thereby prepare an affinity column. Blood was collected from the rabbit to obtain a serum, which was then applied to the affinity column to purify anti-SYNCRIP-N antibody.

(ii) Anti-SUYNCRIP-Pep Antibody

An antibody against a peptide having amino acids 140–152 of SYNCRIP was prepared from rabbits using this peptide (to which a Cys residue was artificially introduced at its N-terminus) crosslinked with keyhole limpet hemocyanin. The anti-peptide antibody (i.e., anti-SYNCRYP-Pep antibody) was affinity-purified with the antigenic peptide-conjugated beads.

Figure 8:
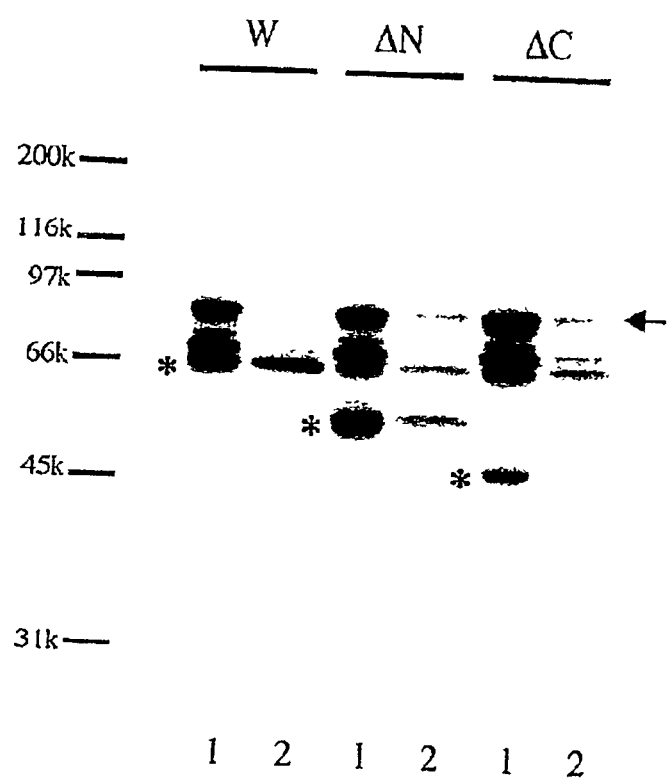
FIG. 8 shows the results of reactivity experiments on antibodies against truncated SYNCRIP proteins (anti-ΔSYNCRIP antibodies).

These antibodies reacted with SYNCRIP and also with hnRNP (82 kDa) and a degradation product thereof (74 kDa) (FIG. 8). When the full-length SYNCRIP cDNA was transfected into COS-7 cells, SYNCRIP was over-expressed and localized in the cytoplasm in both cases examined with anti-SYNCRIP-N antibody and anti-SYNCRIP-Pep antibody (FIGS. 3A–B). Panels A and B in FIG. 3 demonstrated that SYNCRIP is not localized in the nucleus but localized in the cytoplasm. In FIG. 3, panel A is a photograph showing the behavior of SYNCRIP over-expressed in COS-7 cells by the indirect immunofluorescence technique using anti-SYNCRIP-N antibody stained. Panel B is a photograph showing the behavior of SYNCRIP over-expressed in COS-7 cells by indirect immunofluorescence technique using anti SYNCRIP-Pep antibody.

Further, mouse cerebellum was fractionated into a crude nuclear fraction, cytosol fraction, crude microsome fraction and crude synaptic vesicle fraction. Then, the localization of SYNCRIP in each of these fractions was examined. The results are shown in FIG. 4.

Figure 4:
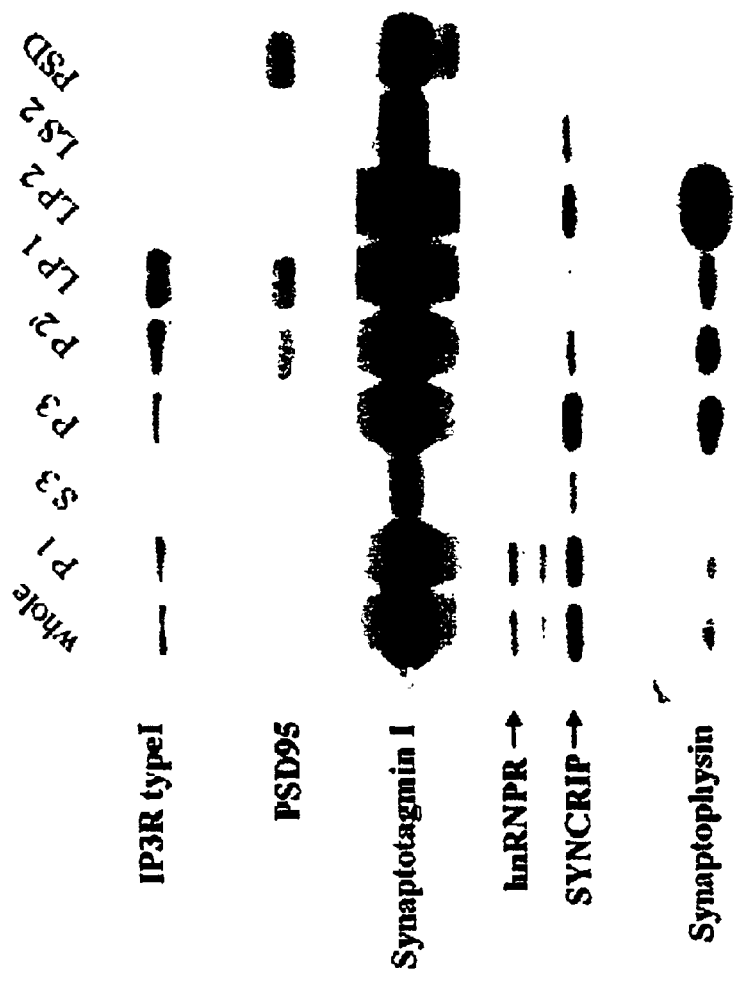
FIG. 4 shows the expression of SYNCRIP in subcellular fractions.

In the lanes in FIG. 4, P1 is a crude nuclear fraction from mouse cerebellum; S3 is a supernatant (cytosol) from nuclear fractionation; P3 is a crude microsome fraction containing vesicles; and P2' is a crude synaptosome fraction. LP1 is a synaptic heavy membrane fraction obtained from synaptosomes lysed in a hypotonic solution; LP2 is a synaptic vesicle fraction; LS2 is a synaptic cytosol fraction; and PSD is a postsynaptic density fraction prepared from LP1 fraction. In FIG. 4, the bands of IP3R Type I indicate inositol 1,4,5 triphosphate receptor I, and serve as a marker for crude microsome fraction. Further, the bands of PSD95 indicate postsynaptic density proteins, and serve as a marker for postsynaptic density fraction.

As seen from FIG. 4, while a SYNCRIP band appeared in the microsome fraction (P3), an hnRNP R band did not appear in the microsome fraction but appeared in the nuclear fraction (P1). Thus, it was demonstrated that these proteins are different in function and behavior.

(2) Time of Expression and Tissue Distribution of SYNCRIP

Figure 5:
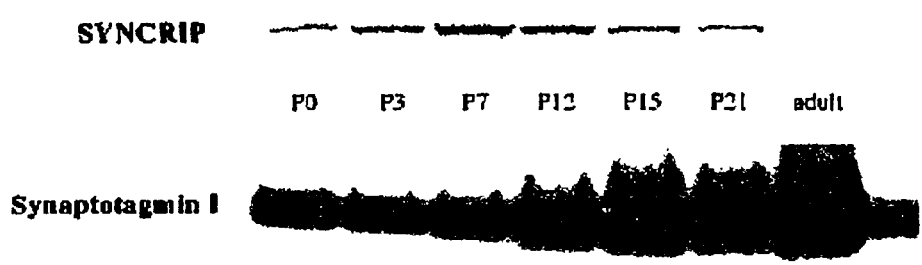
FIG. 5 shows the expression of SYNCRIP during the postnatal development in mouse.

The time of expression of SYNCRIP was determined by preparing cerebellum homogenates from postnatal day 0, 3, 7, 12, 15 and 21 mice and adult mice, and performing Western blotting using anti-SYNCRIP-N antibody. The expression of Syt-I contained in each of the homogenate was also determined. The results are shown in FIG. 5. In FIG. 5, the bands in the upper panel indicate SYNCRIP, and the bands in the lower panel Syt-I.

As seen from FIG. 5, the expression of SYNCRIP in mouse cerebellum during the postnatal development was the highest at P7 (postnatal day 7) and decreased afterward (FIG. 5; upper panel). On the other hand, the expression of Syt-I gradually increased during the development (FIG. 5; lower panel).

Figure 6:
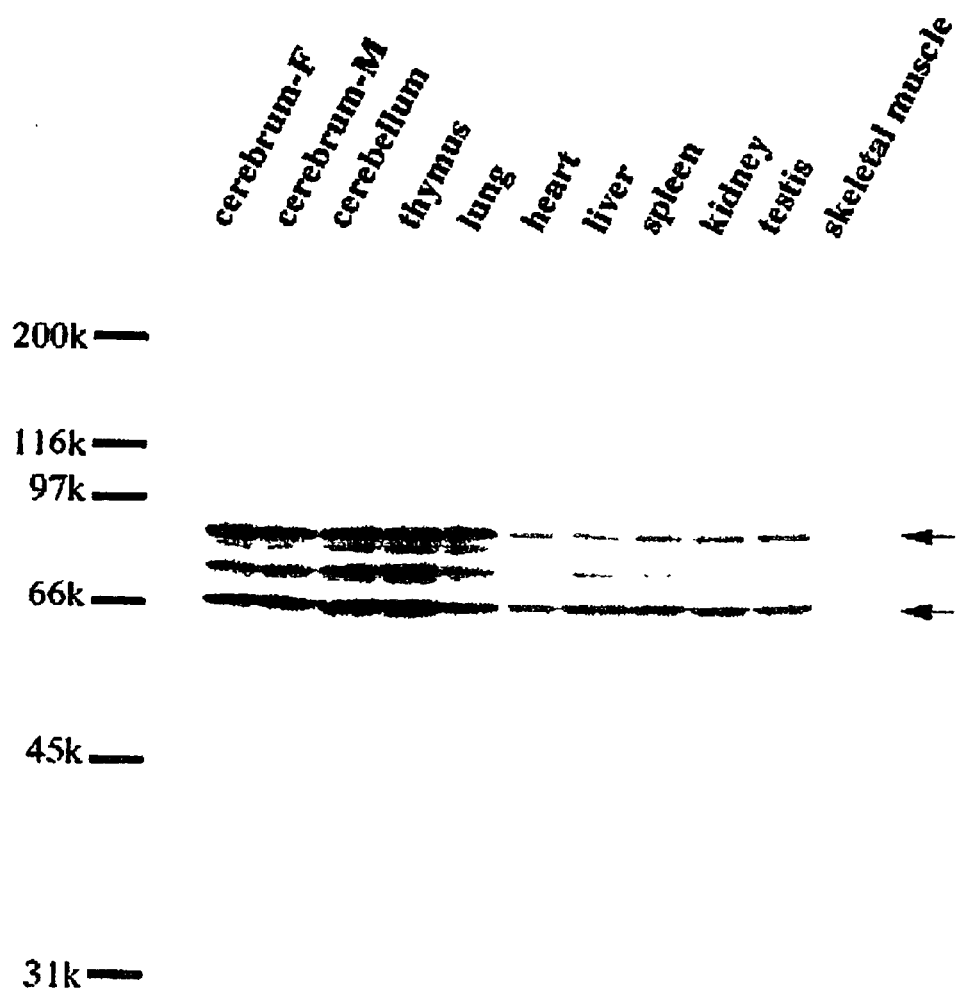
FIG. 6 shows the expression pattern of SYNCRIP in mouse tissues.

Subsequently, tissues expressing SYNCRIP were determined by preparing homogenates (30 μg for each) from individual tissues of postnatal day 7 mice and performing Western blotting using anti-SYNCRIP-Pep antibody. The expression of hnRNP R in individual tissues was also determined. The results are shown in FIG. 6. In FIG. 6, the bands pointed out by the upper arrow indicate hnRNP R (82 kDa), and the bands pointed out by the lower arrow SYN-CRIP (66 kDa).

As seen from FIG. 6, the expression of SYNCRIP (66 kDa) was observed at an almost constant level not only in the central nervous tissues but also in all of the peripheral tissues tested (FIG. 6; lower arrow). The 82 kDa hnRNP R was expressed in parallel with SYNCRIP in various tissues (FIG. 6; upper arrow).

EXAMPLE 3

RNA Binding Assay

In order to examine whether the protein of the invention binds to RNA molecules or not, in vitro RNA binding assay was carried out.

Briefly, [$^{35}$S]-labeled SYNCRIP was prepared by in vitro translation using a TNT-coupled reticulocyte lysate system (Promega). An aliquot of [$^{35}$S]-labeled SYNCRIP was incubated with an indicated amount of poly(A), poly(C) or poly(U) RNA or yeast tRNA in 50 μl of a binding buffer (10 mM Tris-HCl (pH 8.0), 1 mM EDTA and 10 mM NaCl) at 25° C. for 30 min. Then, 50 μl of poly(U)-Sephadex (20% slurry in the binding buffer) was added to each of the mixtures followed by incubation at 25° C. for 45 min. After washing the beads with 500 μl of the binding buffer 4 times, the bound fractions were subjected to 10% SDS-PAGE and analyzed by autoradiography.

Figure 7:
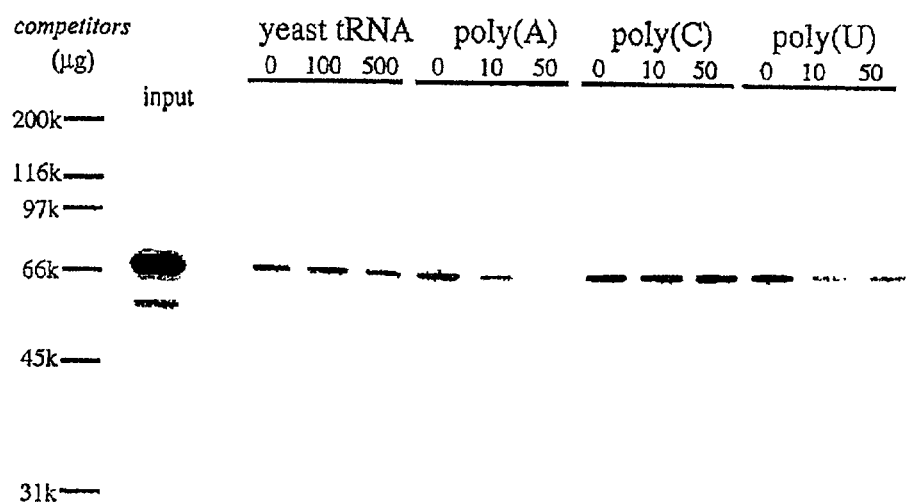
FIG. 7 shows the results of binding experiments between SYNCRIP and RNA molecules.

As shown in FIG. 7, [$^{35}$S]-labeled SYNCRIP indeed bound to poly(U) RNA Sephadex. When poly(A) RNA is not contained in the sample (i.e., poly(A): 0), a strong band appears. When the amount of poly(A) RNA increases (i.e., poly(A): 10 and 50 μg), the band becomes weaker because the binding of the labeled SYNCRIP to the poly(U) RNA on carrier beads is inhibited, which results in liberation of SYNCRIP and its binding to poly(A) RNA (FIG. 7; the three lanes under poly(A)). On the other hand, no changes in the intensity of bands were observed in yeast tRNA and poly(C) RNA. These substances did not compete with the poly(U) RNA on carrier beads for SYNCRIP binding. Thus, it was demonstrated that the protein of the invention, SYNCRIP, binds preferentially to poly(A) RNA.

EXAMPLE 4

In vitro Binding Between SYNCRIP and C2B Domain of Syt

In this Example, in vitro assay was performed to determine which region of SYNCRIP binds to the C2B domain of Synaptotagmin.

(1) The Binding of Full-length or Truncated SYNCRIP Expressed in COS-7 to GST-Syt-II C2B cDNA fragments encoding an N-terminal truncated SYN-CRIP (ΔN; lacking amino acids 1–98 in the full-length amino acid sequence (SEQ ID NO: 4)) (FIG. 1B) and a C-terminal truncated SYNCRIP (ΔC; lacking amino acids 401–561 in the full-length amino acid sequence (SEQ ID NO: 4)) (FIG. 1B), respectively, were transfected into COS-7 cells in the same manner as in Example 2. Using the thus obtained COS-7 cells and the COS-7 cells prepared in Example 2, the binding of the full-length or truncated SYNCRIP proteins to GST-Syt-II C2B was evaluated.

First, a cell lysate was prepared from each of the COS-7 cells expressing individual SYNCRIP proteins by suspending the cells in a cell lysis buffer of the following composition. Then, the cell lysate was centrifuged at 12,000 rpm at 4° C. for 20 min.

Cell lysis buffer: 10 mM Hepes-NaOH (pH 7.4), 100 mM NaCl, 1 mM β-mercaptoethanol, 1 mM EDTA, 1% NP-40, 0.2 mM PMSF, 10 μM leupeptin, and 10 μM pepstatin A.

Each lysate was incubated with an equal amount of GST-Sty-II C2B protein at 4° C. for 2 hr. Then, GST-Sty-II C2B protein-bound fractions were recovered with glutathione-Sepharose and examined by Western blotting using anti-SYNCRIP-Pep antibody. The antibody used in the Western blotting was prepared in Example 2. (In the subsequent Western blotting analyses, the antibodies used were also from Example 2.)

(2) The Binding of Endogenous SYNCRIP from Mouse Brain to Various GST-Syt-II Fusions and the Effect of $Ca^{2+}$ and $Mg^{2+}$ on the Binding Mouse whole brain detergent-extracts (2.5 mg/ml) were prepared in a lysis buffer of the following composition.

Lysis buffer: 10 mM Hepes-NaOH (pH 7.4), 140 mM NaCl, 1% (w/v) Triton X-100, 1 mM β-mercaptoethanol, 1 mM EDTA, 0.2 mM PMSF, 10 μM leupeptin and 10 μM pepstatin A.

To each 3 ml aliquot, EGTA (final concentration: 2 mM), $CaCl_2$ (1 mM), EDTA (2 mM) or $MgCl_2$ (1 mM) was added and incubated with 25 μg of a purified GST-fusion protein with a region of Syt-II or 25 μg of purified GST alone at 4° C. for 2 hr. After addition of 50 μl (50% slurry) of glutathione-Sepharose and another 1 hr incubation, the resins were extensively washed with an extraction buffer containing a chelating agent or divalent ion. The bound proteins were subjected to Western blotting using anti-SYNCRIP-N antibody to examine the binding of SYNCRIP to various regions of Syt-II.

(3) The Binding of Full-length SYNCRIP Expressed in Sf9 Cells to GST-CB2 from Various Syts For the expression of SYNCRIP in an insect cell Sf9, a cDNA fragment encoding full-length SYNCRIP was subcloned into pFASTBAC1 (Life Technology) to create a recombinant bacurovirus carrying SYNCRIP, which was then proliferated in accordance with the manufacturer's instructions. Sf9 cells cultured in TNM-FH medium supplemented with 10% fetal calf serum were infected with the proliferated recombinant virus. Forty-eight hours after the infection, the cells were used in binding experiments.

A cell lysate containing the full-length SYNCRIP expressed in Sf9 cells was prepared in the same manner as described in (1) above. Each aliquot was incubated with 10–20 μg of one of GST fusion proteins with C2B domains from various Syts. The bound proteins were recovered and subjected to Western blotting using anti-SYNCRIP-N antibody to examine the binding of SYNCRIP to C2B domains from various Syts.

(4) The Binding of Purified, $His_6$-tagged C-Terminal Region of SYNCRIP to Purified GST Fusion Proteins with One of the Syt-II C2 Domains A $His_6$-tagged recombinant protein comprising a C-terminal region of SYNCRIP (amino acids 401–561) was expressed in E. coli using pREST plasmid (Invitrogen). The recombinant protein was recovered from inclusion bodies by using a denaturing solution (6 M guanidine-HCl, 10 mM Tris-HCl (pH 8.0), 0.5 M NaCl, 1 mM , β-mercaptoethanol) and purified with ProBond resin. The denatured recombinant protein was refolded by dialysis against 10 mM Tris-HCl (pH 8.0), 10 mM β-mercaptoethanol, 0.1 M NaCl and 1 mM EDTA, with gradual decrease of urea concentration from 6 M to 0.001 M. The dialysate was centrifuged at 12,000 rpm at 4° C. for 20 min to remove the malfolded part and insoluble matter. After aliquots were incubated with various GST-fusion proteins with one of the Syt-II C2 domains, bound proteins were recovered and subjected to Western blotting using anti-Xpress antibody (Invitrogen).

(5) Coimmunoprecipitation Experiments

DNA fragments encoding Syt isoforms tagged with T7-epitope at the N-terminus were transiently transfected into COS cells separately. Forty-eight hours after the transfection, cells were harvested and suspended in a suspension buffer (10 mM Hepes-NaOH (pH 7.4), 100 mM NaCl, 0.5 mM β-mercaptoethanol, 1 mM EDTA, 1% NP-40, 0.2 mM PMSF, 10 μM leupeptin and 10 μM pepstatin). Lysates were prepared by centrifugation of the cell suspension at 12,000 rpm for 20 min and incubated with affinity purified anti-SYNCRIP-N antibody (3.5 μg anibody/1 ml lysate) at 4° C. for 2 hr, followed by another incubation with 10 μl (50% slurry) of protein G-Sepharose (Amersham Pharmacia Biotech) at 4° C. for 1 hr. After washing the beads with the suspension buffer 5 times, the resultant immunoprecipitates were subjected to Western blotting to examine the binding of SYNCRIP to T7-tagged Syt isoforms.

Figure 9:
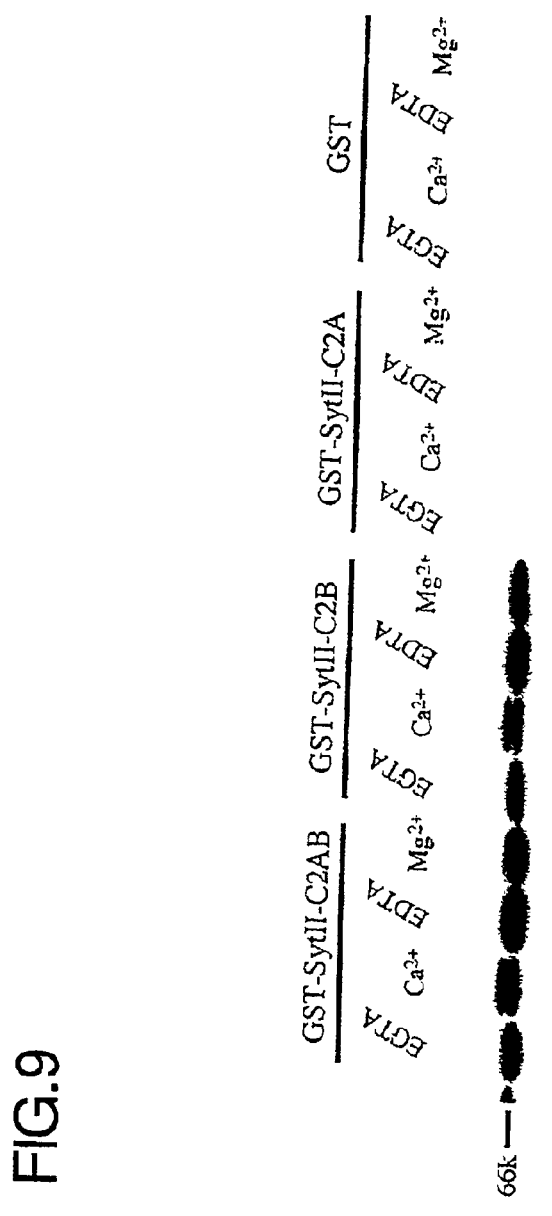

(6) Results (i) SYNCRYP bound to GST-Syt-II C2B and to GST-Syt-II C2AB to an equal extent (FIG. 9). However, SYNCRIP did not bind to GST-Sty-II C2A nor GST alone. This means that the protein of the invention binds to the C2B domain of Synaptotagmin. Further, the above-described binding was independent of $Ca^{2+}$ and $Mg^{2+}$. The evident binding in the presence of 1 mM $MgCl_2$ that is close to the physiological concentration suggested possible similar binding in vivo.

(ii) Full-length (wild type: W), N-terminal truncated (ΔN) and C-terminal truncated (ΔC) SYNCRIP proteins were expressed in COS-7 cells to examine which region of SYNCRIP is important for its binding to Syt. All these constructs were confirmed as being expressed with expected sizes (FIG. 8; see the band marked with "*" in each lane 1). Wild type and ΔN proteins bound to GST-Syt-II C2B as demonstrated by the appearance of a band at the same position as that of the band marked with "*" (FIG. 8; each lane 2). However, ΔC protein did not bind to GST-Syt-II C2B since no band appeared at the position corresponding to mark "*". This result did not change even after reacting ΔC protein with GST-Syt-II C2B for a longer period.

Figure 10:
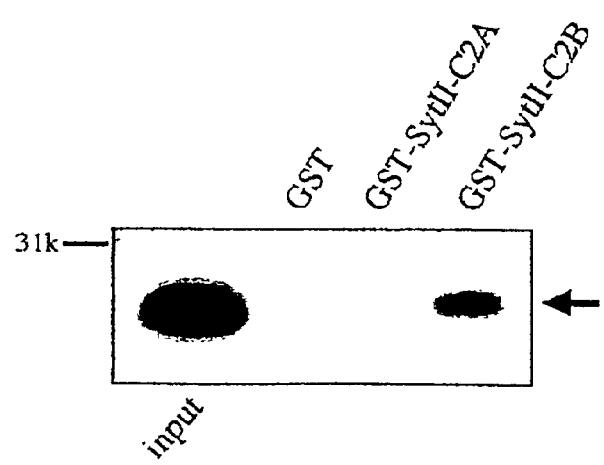
FIG. 10 shows the interaction of a C-terminal region of SYNCRIP with the C2A or C2B domain of Syt.

(iii) The C-terminal region of SYBCRIP prepared in (4) above bound specifically to GST-Syt-II C2B, but did not bind to GST-Syt-II C2A nor GST alone (FIG. 10). These results show that the C-terminal 161 amino acid region spanning from positions 401 to 561 of full-length SYNCRIP (i.e., the amino acid sequence as shown in SEQ ID NO: 2 encoded by the nucleotide sequence of SEQ ID NO: 1) binds to the C2B domain of Syt.

EXAMPLE 5

In vivo Binding Experiment Between SYNCRIP and Syt-I

In this Example, immunohistochemical studies were performed on postnatal day 7 mouse cerebellum in which the expression of SYNCRIP is highest during the postnatal development of mouse cerebellum, in order to examine whether SYNCRIP binds to Syt in vivo.

A DNA fragment encoding SYNCRIP was transfected into COS-7 cells. Forty-eight hours after the transfection, the cells were washed with PBS twice and fixed with 4% paraformaldehyde in PBS at room temperature for 20 min. Fixed cells were permeabilized with 0.1% Triton X-100 in PBS for 5 min and immediately washed with PBS 3 times. After blocking with 2% normal goat serum in PBS, cells were incubated with anti-SYNCRIP-N antibody (0.27 μg/ml) or anti-SYNCRIP-Pep antibody (0.55 μg/ml) in the blocking buffer at room temperature for 1 hr. After washing with PBS 5 times, the cells were incubated with FITC-conjugated goat anti-rabbit IgG (Vector, Burlingame, Calif.). For native tissues, postnatal day 7 ICR mice were perfused with 4% paraformaldehyde in PBS(−). The brains were excised and immersed in the same fixative for 2 hr, and then cryosectioned (8 μm thick). Each section was dried and rehydrated in PBS followed by immunoreaction. Immunofluorescence was observed using a Zeiss Axiophot epifluorescence microscope. The specificity of SYNCRIP immunoreactivity was confirmed by a parallel experiment using a pre-immune serum or anti-SYNCRIP antibody pre-incubated with an excessive amount of the antigenic polypeptide.

Figure 11:
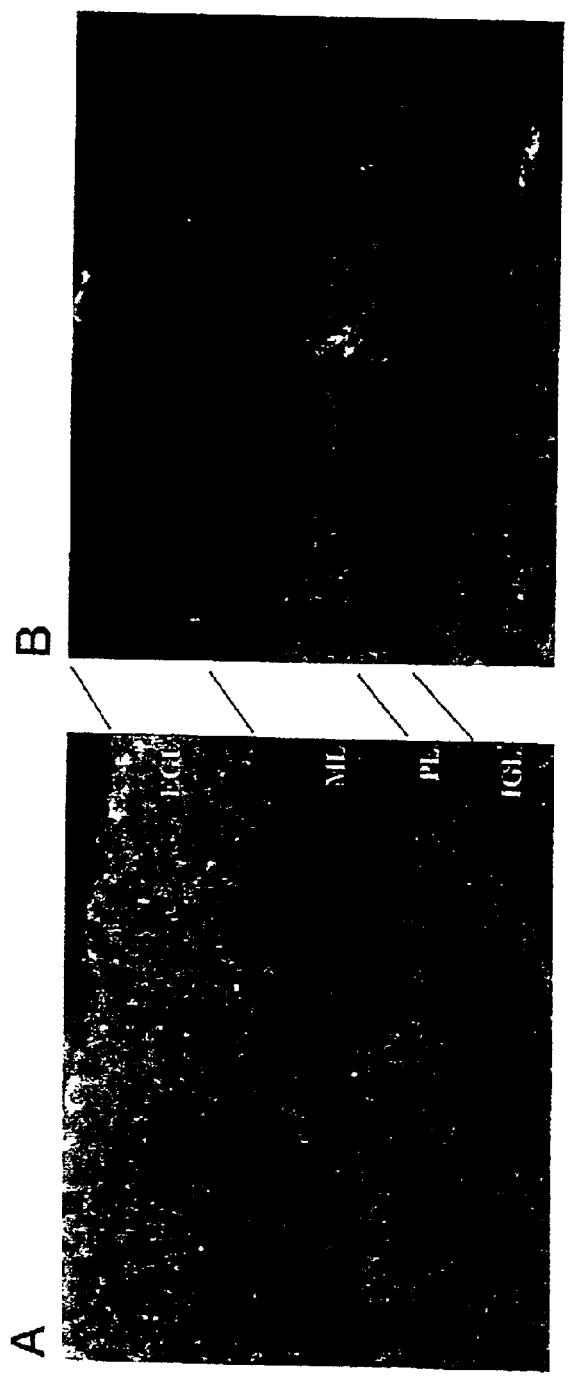
FIG. 11 shows the results of an immunohistochemical assay. The same cryosection was probed with anti-SYNCRIP-N antibody (panel A) and anti-Syt-I antibody (panel B). EGL: external germinal layer; ML: molecular layer; PL: Purkinje cell layer; IGL: internal granule layer.

As a result, SYNCRIP was expressed in most neurons, i.e. granule cells in both external germinal layer and internal granular layer, and Purkinje cells (FIG. 11). In the biochemical fractionation study described earlier, a significant amount of SYNCRIP was observed in LP2 fraction that is a representative synaptic vesicle-rich fraction morphologically (FIG. 4). However, where dendrites of Purkinje cells and synaptic structures concentrated and Syt-I signals were highly positive, anti-SYNCRIP-N antibody-reactive signals concentrated in perinuclear and somatic regions of granule cells and Purkinje cells, and were almost absent in the molecular layer without migrating granule cells therein (FIG. 11A, the region indicated as "ML").

The parallel experiment with anti-SYNCRIP-Pep antibody showed that the immunoreactive signals were exclusively apparent in nuclei, suggesting that the perinuclear and somatic immunosignals with anti-SYNCRIP-N antibody indeed represented the SYNCRIP localization in neurons and that the SYNCRIP signals detected in LP2 fraction by the fractionation study might be derived from SYNCRIP on other membrane structure rather than synaptic vesicles.

EXAMPLE 6

Interaction of SYNCRIP with Various Syt Isoforms

Since SYNCRIPT is expressed in every step of neurodevelopment and expressed ubiquitously in a wide variety of tissues, it is believed that the targets of SYNCRIP are not only the major Syt isoforms (Syt-I and Syt-II), but also other Syt isoforms. Then, the present inventor performed binding experiments between SYNCRIP and 11 Syt isoforms.

Briefly, SYNCRIP was expressed in Sf9 cells (see Section (3) of Example 4). After preparation of a lysate from the cells, each aliquot was incubated with an almost equal volume of GST-Syt-C2B. The binding of SYNCRIP to GST-Syt-C2B was detected by immunoprecipitation using anti-SYNCRIP-N antibody.

Figure 12:
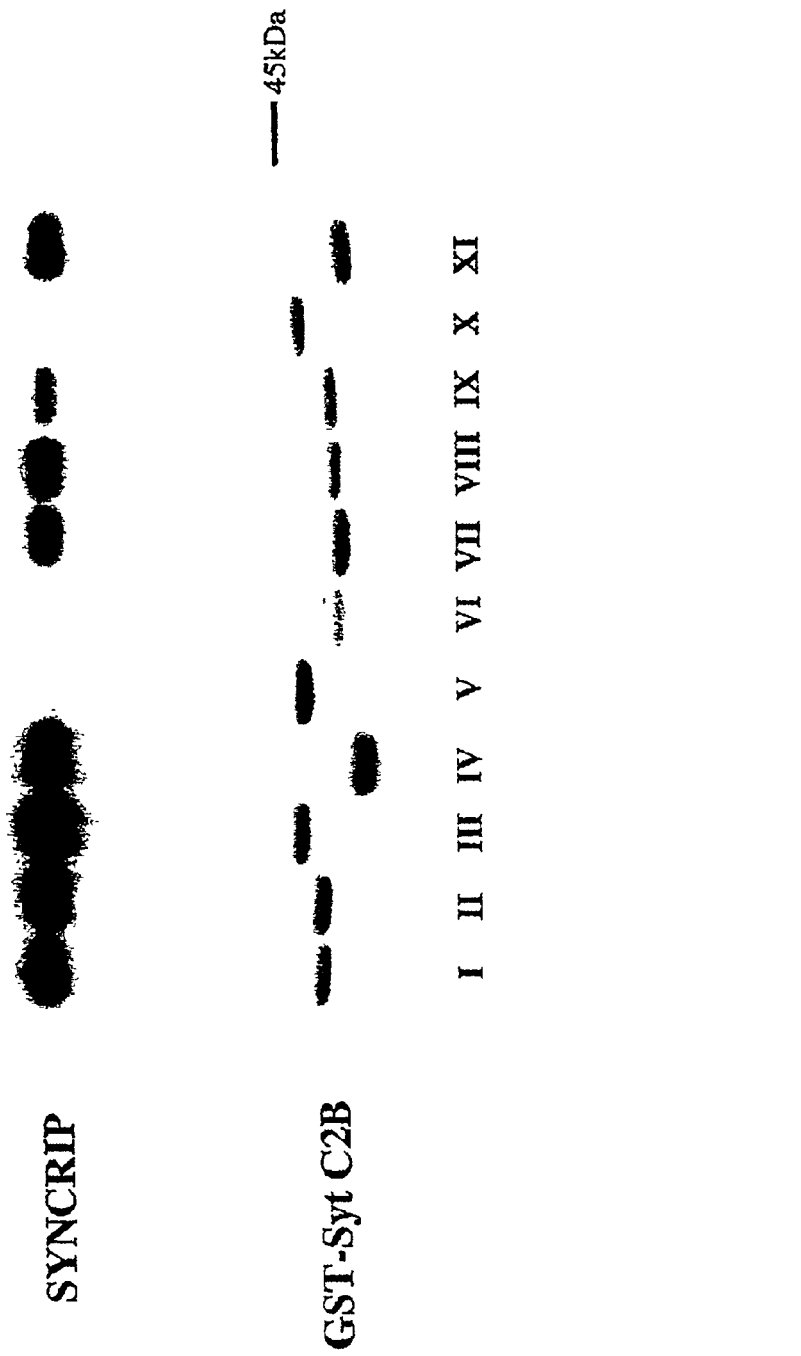
FIG. 12 shows the interaction of SYNCRIP with Syt isoforms.

The results revealed that SYNCRIP binds to the C2B domains of Syt-III, -IV, -VII, -VIII, -IX and -XI in addition to Syt-I and -II (FIG. 12).

EXAMPLE 7

Interaction of SYNCRIP with Syt-VII, -VIII and -IX in Cells

The finding of ubiquitous tissue distribution of SYNCRIP (FIG. 6) led the inventor to focus on ubiquitous isoforms of Syt as physiological targets of SYNCRIP. Thus, the inventor examined the interaction of SYNCRIP with ubiquitous isoforms of Syt in cells by immunoprecipitation.

Figure 13:
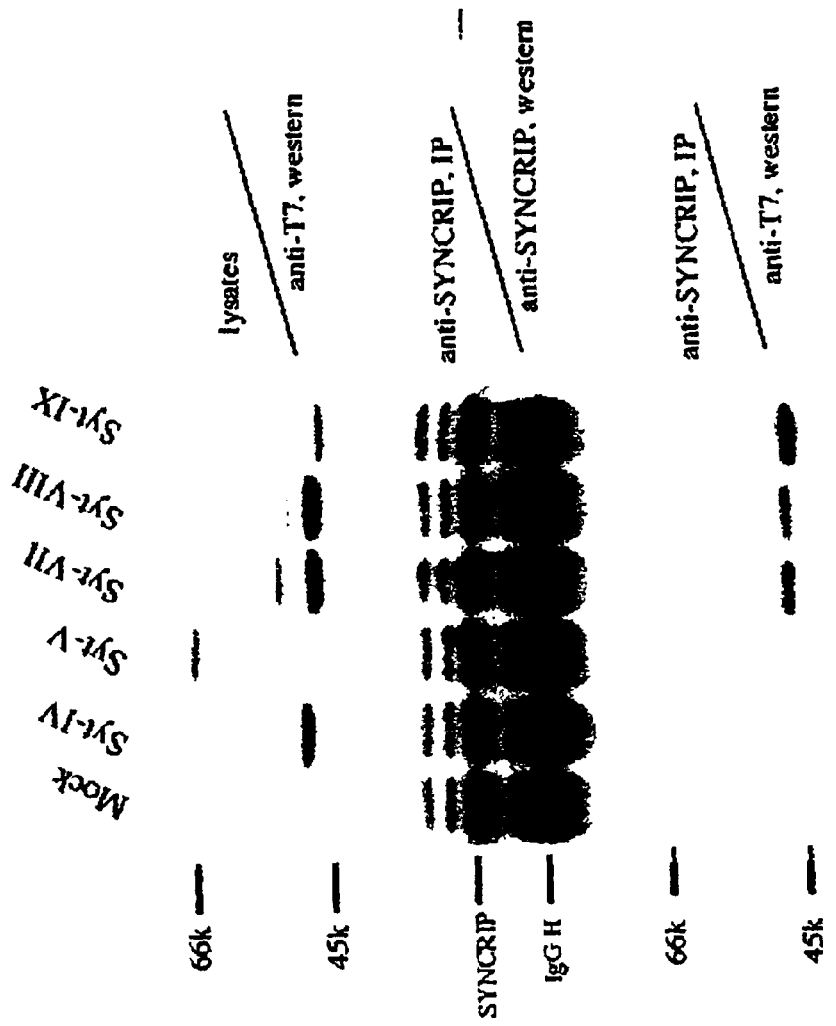
FIG. 13 shows the interaction of SYNCRIP with Syt isoforms in cells.

Briefly, T7-epitope-tagged full-length Syt-IV, -V, -VII, -VIII and -IX were transiently expressed in COS-7 cells. Lysates were prepared from COS-7 cells and immunoprecipitated with anti-SYNCRIP-N antibody. The immunoprecipitates were examined by Western blotting with both anti-SYNCRIP-N antibody (FIG. 13; middle panel) and anti-T7 antibody (FIG. 13; lower panel). The detection of T7-tagged Syt isoforms (Syt-IV, -VII, -VIII and -IX) by Western blotting with anti-T7 antibody confirmed that they were expressed at almost equal levels (FIG. 13; upper panel). The results of immunoblotting of the immunoprecipitates using anti-SYNCRIP-N antibody revealed that SYNCRIP is constantly expressed (FIG. 13; middle panel). The results of immunoblotting of the immunoprecipitates using anti-T7 antibody revealed that Syt-VII, -VIII and -IX were specifically coimmunoprecipitated with SYNCRIP (FIG. 13; lower panel).

Accordingly, it was demonstrated that the ubiquitous isoforms of Syt (i.e., Syt-VII, -VIII and -IX) are the target of SYNCRIP under physiological conditions.

EFFECT OF THE INVENTION

According to the present invention, RNA-binding proteins are provided. Since the protein of the invention is able to bind to Synaptotagmin on synaptic vesicles, the protein is useful as an agent for regulating neurotransmission.

SEQUENCE LISTING FREE TEXT

SEQ ID NO: 8: n represents a, g, c or t (location: 3).
SEQ ID NO: 8: n represents a, g, c or t (location: 6).
SEQ ID NO: 8: n represents a, g, c or t (location: 12).
SEQ ID NO: 8: n represents a, g, c or t (location: 15).
SEQ ID NO: 8: synthetic DNA
SEQ ID NO: 9: n represents a, g, c or t (location: 10).
SEQ ID NO: 9: synthetic DNA

What is claimed is:

1. An isolated nucleic acid molecule encoding a protein comprising the amino acid sequence as shown in SEQ ID NO:4.

2. An isolated nucleic acid molecule comprising a DNA that comprises a nucleotide sequence spanning from position 154 to position 1836 of SEQ ID NO:3.

3. A recombinant vector comprising the nucleic acid molecule according to claim 1.

4. A recombinant vector comprising the nucleic acid molecule according to claim 2.

* * * * *

SEQUENCE LISTING

```
<160> NUMBER OF SEQ ID NOS: 11

<210> SEQ ID NO 1
<211> LENGTH: 483
<212> TYPE: DNA
<213> ORGANISM: Mus musculus
<220> FEATURE:
<221> NAME/KEY: CDS
<222> LOCATION: (1)..(483)

<400> SEQUENCE: 1 att gaa att gtt ttt gct aag cca cca gat cag aag agg aaa gaa aga        48
Ile Glu Ile Val Phe Ala Lys Pro Pro Asp Gln Lys Arg Lys Glu Arg
  1               5                  10                  15 aaa gct cag agg caa gca gca aag aat caa atg tat gat gat tac tac        96
Lys Ala Gln Arg Gln Ala Ala Lys Asn Gln Met Tyr Asp Asp Tyr Tyr
             20                  25                  30 tat tat ggt cca cct cat atg cct ccc cca aca aga ggt cga ggg cgt       144
Tyr Tyr Gly Pro Pro His Met Pro Pro Pro Thr Arg Gly Arg Gly Arg
         35                  40                  45 gga ggt aga ggt ggc tat gga tat cct cca gat tat tat gga tac gaa       192
Gly Gly Arg Gly Gly Tyr Gly Tyr Pro Pro Asp Tyr Tyr Gly Tyr Glu
     50                  55                  60 gat tat tat gat tat tat ggt tat gat tac cat aac tat cgt ggt gga       240
Asp Tyr Tyr Asp Tyr Tyr Gly Tyr Asp Tyr His Asn Tyr Arg Gly Gly
```

-continued

| | | | | | | | | | | | | | | | |
|---|---|---|---|---|---|---|---|---|---|---|---|---|---|---|---|
| tat | gaa | gat | cca | tac | tat | ggt | tat | gaa | gat | ttt | caa | gtt | gga | gct | aga | 288 |
| Tyr | Glu | Asp | Pro | Tyr | Tyr | Gly | Tyr | Glu | Asp | Phe | Gln | Val | Gly | Ala | Arg |
| | | | 85 | | | | | 90 | | | | | 95 | | |

| gga | agg | ggt | ggt | aga | gga | gca | agg | ggt | gct | gct | cca | tcc | aga | ggt | cgt | 336 |
| Gly | Arg | Gly | Gly | Arg | Gly | Ala | Arg | Gly | Ala | Ala | Pro | Ser | Arg | Gly | Arg |
| | | 100 | | | | | 105 | | | | | 110 | | | |

| ggg | gct | gct | cct | ccc | cgt | ggt | aga | gcc | ggt | tat | tca | cag | aga | gga | ggc | 384 |
| Gly | Ala | Ala | Pro | Pro | Arg | Gly | Arg | Ala | Gly | Tyr | Ser | Gln | Arg | Gly | Gly |
| | 115 | | | | | 120 | | | | | 125 | | | | |

| cct | gga | tca | gca | aga | ggc | gtt | cgc | ggt | gcg | aga | gga | ggt | gcc | caa | caa | 432 |
| Pro | Gly | Ser | Ala | Arg | Gly | Val | Arg | Gly | Ala | Arg | Gly | Gly | Ala | Gln | Gln |
| 130 | | | | | 135 | | | | | 140 | | | | | |

| caa | aga | ggc | cgc | ggg | gga | aaa | ggg | gtc | gag | gcc | ggt | cct | gac | ctg | tta | 480 |
| Gln | Arg | Gly | Arg | Gly | Gly | Lys | Gly | Val | Glu | Ala | Gly | Pro | Asp | Leu | Leu |
| 145 | | | | 150 | | | | | 155 | | | | | 160 | |

| caa | | | | | | | | | | | | | | | | 483 |
| Gln | | | | | | | | | | | | | | | | |

<210> SEQ ID NO 2
<211> LENGTH: 161
<212> TYPE: PRT
<213> ORGANISM: Mus musculus

<400> SEQUENCE: 2

```
Ile Glu Ile Val Phe Ala Lys Pro Pro Asp Gln Lys Arg Lys Glu Arg
  1               5                  10                  15

Lys Ala Gln Arg Gln Ala Ala Lys Asn Gln Met Tyr Asp Asp Tyr Tyr
             20                  25                  30

Tyr Tyr Gly Pro Pro His Met Pro Pro Thr Arg Gly Arg Gly Arg
         35                  40                  45

Gly Gly Arg Gly Gly Tyr Gly Tyr Pro Pro Asp Tyr Tyr Gly Tyr Glu
     50                  55                  60

Asp Tyr Tyr Asp Tyr Tyr Gly Tyr Asp Tyr His Asn Tyr Arg Gly Gly
 65                  70                  75                  80

Tyr Glu Asp Pro Tyr Tyr Gly Tyr Glu Asp Phe Gln Val Gly Ala Arg
                 85                  90                  95

Gly Arg Gly Gly Arg Gly Ala Arg Gly Ala Ala Pro Ser Arg Gly Arg
            100                 105                 110

Gly Ala Ala Pro Pro Arg Gly Arg Ala Gly Tyr Ser Gln Arg Gly Gly
        115                 120                 125

Pro Gly Ser Ala Arg Gly Val Arg Gly Ala Arg Gly Gly Ala Gln Gln
    130                 135                 140

Gln Arg Gly Arg Gly Gly Lys Gly Val Glu Ala Gly Pro Asp Leu Leu
145                 150                 155                 160

Gln
```

<210> SEQ ID NO 3
<211> LENGTH: 3452
<212> TYPE: DNA
<213> ORGANISM: Mus musculus
<220> FEATURE:
<221> NAME/KEY: CDS
<222> LOCATION: (154)..(1839)

<400> SEQUENCE: 3
gcgggtttgc tgccagcggc gtgagcttcg gccgccattt tacaacagct ccactcgcgc    60
cggacacagg gagcagcgag cacgcgttcc ccgccagccg acccggtcgg acggattcct   120

-continued

```
cggccccagc cccgcgggga gatctctgga aac atg gct aca gaa cat gtt aat      174
                                 Met Ala Thr Glu His Val Asn
                                  1               5 gga aat ggt act gaa gag ccc atg gat act act tca gca gtt atc cat       222
Gly Asn Gly Thr Glu Glu Pro Met Asp Thr Thr Ser Ala Val Ile His
         10              15                  20 tca gaa aat ttt cag aca ttg ctt gat gct ggt tta cca cag aaa gtt       270
Ser Glu Asn Phe Gln Thr Leu Leu Asp Ala Gly Leu Pro Gln Lys Val
     25                  30                  35 gct gaa aaa cta gat gaa att tac gtt gca ggg cta gtt gca cat agt       318
Ala Glu Lys Leu Asp Glu Ile Tyr Val Ala Gly Leu Val Ala His Ser
 40                  45                  50                  55 gat tta gat gaa aga gct atc gaa gct tta aaa gag ttc aat gaa gac       366
Asp Leu Asp Glu Arg Ala Ile Glu Ala Leu Lys Glu Phe Asn Glu Asp
                 60                  65                  70 ggc gca ttg gca gtg ctt caa cag ttt aaa gac agt gat ctc tct cat       414
Gly Ala Leu Ala Val Leu Gln Gln Phe Lys Asp Ser Asp Leu Ser His
             75                  80                  85 gtt cag aac aaa agt gcc ttt tta tgt gga gtc atg aag act tac agg       462
Val Gln Asn Lys Ser Ala Phe Leu Cys Gly Val Met Lys Thr Tyr Arg
         90                  95                  100 cag aga gaa aaa cag ggg acc aaa gta gca gac tct agt aaa gga cca       510
Gln Arg Glu Lys Gln Gly Thr Lys Val Ala Asp Ser Ser Lys Gly Pro
     105                 110                 115 gat gag gca aag att aag gca ctt ttg gaa aga aca ggc tac aca ctt       558
Asp Glu Ala Lys Ile Lys Ala Leu Leu Glu Arg Thr Gly Tyr Thr Leu
120                 125                 130                 135 gat gtg act aca ggt cag agg aag tat gga gga cca cct cca gat tcc       606
Asp Val Thr Thr Gly Gln Arg Lys Tyr Gly Gly Pro Pro Pro Asp Ser
                 140                 145                 150 gtt tat tca ggt cag cag cct tct gtt ggc act gag ata ttt gtg ggg       654
Val Tyr Ser Gly Gln Gln Pro Ser Val Gly Thr Glu Ile Phe Val Gly
             155                 160                 165 aag atc ccc aga gat ctg ttt gag gat gag ctt gtt cca tta ttt gag       702
Lys Ile Pro Arg Asp Leu Phe Glu Asp Glu Leu Val Pro Leu Phe Glu
         170                 175                 180 aaa gct gga cct ata tgg gat ctt cgt tta atg atg gat ccg ctc act       750
Lys Ala Gly Pro Ile Trp Asp Leu Arg Leu Met Met Asp Pro Leu Thr
     185                 190                 195 ggt ctc aac aga ggt tat gcg ttt gtc act ttt tgt aca aaa gaa gca       798
Gly Leu Asn Arg Gly Tyr Ala Phe Val Thr Phe Cys Thr Lys Glu Ala
200                 205                 210                 215 gca caa gag gct gtt aaa ctg tat aat aat cat gaa att cgt tcc ggg       846
Ala Gln Glu Ala Val Lys Leu Tyr Asn Asn His Glu Ile Arg Ser Gly
                 220                 225                 230 aag cac att ggt gtc tgc atc tca gtt gcc aac aat agg ctt ttt gtg       894
Lys His Ile Gly Val Cys Ile Ser Val Ala Asn Asn Arg Leu Phe Val
             235                 240                 245 ggc tcg att cct aag agt aaa acc aag gag cag att ctt gag gaa ttt       942
Gly Ser Ile Pro Lys Ser Lys Thr Lys Glu Gln Ile Leu Glu Glu Phe
         250                 255                 260 agc aaa gtg aca gag ggt ctc aca gat gtc att tta tac cac caa cct       990
Ser Lys Val Thr Glu Gly Leu Thr Asp Val Ile Leu Tyr His Gln Pro
     265                 270                 275 gat gac aag aaa aaa aac aga ggc ttt tgc ttt ctt gaa tat gaa gat       1038
Asp Asp Lys Lys Lys Asn Arg Gly Phe Cys Phe Leu Glu Tyr Glu Asp
280                 285                 290                 295 cac aaa aca gct gcc cag gca aga cgt agg cta atg agt ggt aaa gtc      1086
His Lys Thr Ala Ala Gln Ala Arg Arg Arg Leu Met Ser Gly Lys Val
```

```
                    300             305             310
aaa gtc tgg gga aat gtt gga act gtt gag tgg gct gat cct att gaa    1134
Lys Val Trp Gly Asn Val Gly Thr Val Glu Trp Ala Asp Pro Ile Glu
            315                 320                 325 gat cct gat cct gaa gtt atg gca aag gta aaa gtg ctg ttt gta cgc    1182
Asp Pro Asp Pro Glu Val Met Ala Lys Val Lys Val Leu Phe Val Arg
            330                 335                 340 aac ctt gcc aac acg gta aca gaa gaa att tta gaa aag tca ttt agt    1230
Asn Leu Ala Asn Thr Val Thr Glu Glu Ile Leu Glu Lys Ser Phe Ser
            345                 350                 355 cag ttt ggg aaa ctg gaa cga gta aag aag cta aaa gat tat gct ttc    1278
Gln Phe Gly Lys Leu Glu Arg Val Lys Lys Leu Lys Asp Tyr Ala Phe
360                 365                 370                 375 att cat ttt gat gag aga gat ggt gct gtc aag gct atg gaa gaa atg    1326
Ile His Phe Asp Glu Arg Asp Gly Ala Val Lys Ala Met Glu Glu Met
                380                 385                 390 aat ggt aaa gac ttg gag gga gaa aat att gaa att gtt ttt gct aag    1374
Asn Gly Lys Asp Leu Glu Gly Glu Asn Ile Glu Ile Val Phe Ala Lys
            395                 400                 405 cca cca gat cag aag agg aaa gaa aga aaa gct cag agg caa gca gca    1422
Pro Pro Asp Gln Lys Arg Lys Glu Arg Lys Ala Gln Arg Gln Ala Ala
            410                 415                 420 aag aat caa atg tat gat gat tac tac tat tat ggt cca cct cat atg    1470
Lys Asn Gln Met Tyr Asp Asp Tyr Tyr Tyr Tyr Gly Pro Pro His Met
425                 430                 435 cct ccc cca aca aga ggt cga ggg cgt gga ggt aga ggt ggc tat gga    1518
Pro Pro Pro Thr Arg Gly Arg Gly Arg Gly Gly Arg Gly Gly Tyr Gly
440                 445                 450                 455 tat cct cca gat tat tat gga tac gaa gat tat tat gat tat tat ggt    1566
Tyr Pro Pro Asp Tyr Tyr Gly Tyr Glu Asp Tyr Tyr Asp Tyr Tyr Gly
                460                 465                 470 tat gat tac cat aac tat cgt ggt gga tat gaa gat cca tac tat ggt    1614
Tyr Asp Tyr His Asn Tyr Arg Gly Gly Tyr Glu Asp Pro Tyr Tyr Gly
            475                 480                 485 tat gaa gat ttt caa gtt gga gct aga gga agg ggt ggt aga gga gca    1662
Tyr Glu Asp Phe Gln Val Gly Ala Arg Gly Arg Gly Gly Arg Gly Ala
            490                 495                 500 agg ggt gct gct cca tcc aga ggt cgt ggg gct gct cct ccc cgt ggt    1710
Arg Gly Ala Ala Pro Ser Arg Gly Arg Gly Ala Ala Pro Pro Arg Gly
505                 510                 515 aga gcc ggt tat tca cag aga gga ggc cct gga tca gca aga ggc gtt    1758
Arg Ala Gly Tyr Ser Gln Arg Gly Gly Pro Gly Ser Ala Arg Gly Val
520                 525                 530                 535 cgc ggt gcg aga gga ggt gcc caa caa caa aga ggc cgc ggg gga aaa    1806
Arg Gly Ala Arg Gly Gly Ala Gln Gln Gln Arg Gly Arg Gly Gly Lys
                540                 545                 550 ggg gtc gag gcc ggt cct gac ctg tta caa tga agactgactt gctattgtgg    1859
Gly Val Glu Ala Gly Pro Asp Leu Leu Gln
            555                 560 gattacacca gaagcttgca gtggagtaat ggtaaggaaa atcaagcaac cttaaatatc    1919
tcggatgtat aggagcatat tctattgcag aagaccctcc tatgaagatc atggaatcaa    1979
atacgggaca ttgaactaat acttggactt tgttatgaat ttctttaaca attttctctg    2039
cagtgcaagt tattaaacta aagctactct attttccaaa tgtgttccaa aaaaatcctt    2099
cataacttct agcatggtat cttaataaag aataaagttg ttctctttaa aaaatctgct    2159
ctaagtagat ttttcccctc ttttttaatt aaggatctca gcagtggtat ctgaaatat    2219 tctcttgaat ttgtgcattt aaatttattt gcagtgatac agatgccact gttggtaccc    2279
```

```
ttaaattttt atttctgctc accaaggtta atcatgattg tctatatctt ttttatagta    2339
atcacttttg aattgtgttc agatgcagtt tcaggtgtaa tcatcagagc tggttagtca    2399
ggcattccag atagtggttc ttttcagaac cttttaaag ggttggttaa ctacctcagt     2459
agcagaggat tgaactatac cctgtctgta ctgtacatag aaaatctttg tagataaaag    2519
caaggcttgt taaatgat atgagggtaa gattttaata taccaaatgt aacattctta      2579
gttgccttta gtttcagagg cttgtaagac ttcctcatga ccatcataac aggccttgct    2639
tttgtcgtat tttgtggctg aaaaagcagc cttgcttctt cagatattgt agttatttgg    2699
atgtataata gtttagcaag atgttacttt tgtaagacat cagatgttca aaaaaaagt     2759 gcatccgaac ttgtactaaa tactgcagtg tccctttata aaaagtcaga ctaaaactga    2819
caattgtaca gcaaagcctg acatttggat attttgaagt ttttcataa atcatagaaa     2879 ttagtatatg gctgtagttt agctttttag gtaaaggta tgtttcatta gtgcatttgt      2939
tattgctgat cactataaaa atgtgaatca gctttccatt tcttatgcag gtcatgataa    2999
cttgtagaat agagtacaat catttgtgct atgttttttaa ttttctaaag cacccttgatg   3059 acaatgagtg ttcagtggtg aagcatcctc tattgaatca ccctcaaaaa attttttttgc    3119 caagtcctaa gttgatagct taaagtcaaa agtaaaatta tagtttaagt aggacttggt     3179
gtaaagaaac ccctcccccc ttccccaaag ggatactgca gttctatcac acacccagta    3239
ggcaccacga tgacgatcag agctagacct gactaaggtt ttatacacac cagttccca     3299 gtaaatgcaa atttaacaag aaaattagac atgtcatatg ttcaaaatgc tcatggcaaa    3359
caatcatttt gcattcctgc aaataaaatt gttttatacc agcttggact taaccaggct    3419
gaacttgcta atcggatccc cgggtaccga gct                                 3452
```

<210> SEQ ID NO 4
<211> LENGTH: 561
<212> TYPE: PRT
<213> ORGANISM: Mus musculus

<400> SEQUENCE: 4

```
Met Ala Thr Glu His Val Asn Gly Asn Gly Thr Glu Pro Met Asp
  1               5                  10                  15

Thr Thr Ser Ala Val Ile His Ser Glu Asn Phe Gln Thr Leu Leu Asp
                 20                  25                  30

Ala Gly Leu Pro Gln Lys Val Ala Glu Lys Leu Asp Glu Ile Tyr Val
             35                  40                  45

Ala Gly Leu Val Ala His Ser Asp Leu Asp Glu Arg Ala Ile Glu Ala
         50                  55                  60

Leu Lys Glu Phe Asn Glu Asp Gly Ala Leu Ala Val Leu Gln Gln Phe
 65                  70                  75                  80

Lys Asp Ser Asp Leu Ser His Val Gln Asn Lys Ser Ala Phe Leu Cys
                     85                  90                  95

Gly Val Met Lys Thr Tyr Arg Gln Arg Glu Lys Gln Gly Thr Lys Val
                100                 105                 110

Ala Asp Ser Ser Lys Gly Pro Asp Glu Ala Lys Ile Lys Ala Leu Leu
            115                 120                 125

Glu Arg Thr Gly Tyr Thr Leu Asp Val Thr Thr Gly Gln Arg Lys Tyr
        130                 135                 140

Gly Gly Pro Pro Pro Asp Ser Val Tyr Ser Gly Gln Gln Pro Ser Val
145                 150                 155                 160
```

-continued

```
Gly Thr Glu Ile Phe Val Gly Lys Ile Pro Arg Asp Leu Phe Glu Asp
            165                 170                 175

Glu Leu Val Pro Leu Phe Glu Lys Ala Gly Pro Ile Trp Asp Leu Arg
        180                 185                 190

Leu Met Met Asp Pro Leu Thr Gly Leu Asn Arg Gly Tyr Ala Phe Val
    195                 200                 205

Thr Phe Cys Thr Lys Glu Ala Ala Gln Glu Ala Val Lys Leu Tyr Asn
210                 215                 220

Asn His Glu Ile Arg Ser Gly Lys His Ile Gly Val Cys Ile Ser Val
225                 230                 235                 240

Ala Asn Asn Arg Leu Phe Val Gly Ser Ile Pro Lys Ser Lys Thr Lys
                245                 250                 255

Glu Gln Ile Leu Glu Glu Phe Ser Lys Val Thr Glu Gly Leu Thr Asp
            260                 265                 270

Val Ile Leu Tyr His Gln Pro Asp Asp Lys Lys Asn Arg Gly Phe
        275                 280                 285

Cys Phe Leu Glu Tyr Glu Asp His Lys Thr Ala Ala Gln Ala Arg Arg
    290                 295                 300

Arg Leu Met Ser Gly Lys Val Lys Val Trp Gly Asn Val Gly Thr Val
305                 310                 315                 320

Glu Trp Ala Asp Pro Ile Glu Asp Pro Asp Pro Glu Val Met Ala Lys
                325                 330                 335

Val Lys Val Leu Phe Val Arg Asn Leu Ala Asn Thr Val Thr Glu Glu
            340                 345                 350

Ile Leu Glu Lys Ser Phe Ser Gln Phe Gly Lys Leu Glu Arg Val Lys
        355                 360                 365

Lys Leu Lys Asp Tyr Ala Phe Ile His Phe Asp Glu Arg Asp Gly Ala
    370                 375                 380

Val Lys Ala Met Glu Glu Met Asn Gly Lys Asp Leu Glu Gly Glu Asn
385                 390                 395                 400

Ile Glu Ile Val Phe Ala Lys Pro Pro Asp Gln Lys Arg Lys Glu Arg
                405                 410                 415

Lys Ala Gln Arg Gln Ala Ala Lys Asn Gln Met Tyr Asp Asp Tyr Tyr
            420                 425                 430

Tyr Tyr Gly Pro Pro His Met Pro Pro Thr Arg Gly Arg Gly Arg
        435                 440                 445

Gly Gly Arg Gly Gly Tyr Gly Tyr Pro Pro Asp Tyr Gly Tyr Glu
    450                 455                 460

Asp Tyr Tyr Asp Tyr Tyr Gly Tyr Asp Tyr His Asn Tyr Arg Gly Gly
465                 470                 475                 480

Tyr Glu Asp Pro Tyr Tyr Gly Tyr Glu Asp Phe Gln Val Gly Ala Arg
                485                 490                 495

Gly Arg Gly Gly Arg Gly Ala Arg Gly Ala Pro Ser Arg Gly Arg
            500                 505                 510

Gly Ala Ala Pro Pro Arg Gly Arg Ala Gly Tyr Ser Gln Arg Gly Gly
        515                 520                 525

Pro Gly Ser Ala Arg Gly Val Arg Gly Ala Arg Gly Ala Gln Gln
    530                 535                 540

Gln Arg Gly Arg Gly Gly Lys Gly Val Glu Ala Gly Pro Asp Leu Leu
545                 550                 555                 560

Gln
```

<210> SEQ ID NO 5

```
<211> LENGTH: 17
<212> TYPE: PRT
<213> ORGANISM: Mus musculus

<400> SEQUENCE: 5

Val Thr Glu Gly Leu Thr Asp Val Ile Leu Tyr His Gln Pro Asp Asp
 1               5                  10                  15
Lys

<210> SEQ ID NO 6
<211> LENGTH: 6
<212> TYPE: PRT
<213> ORGANISM: Mus musculus

<400> SEQUENCE: 6

Val Thr Glu Gly Leu Thr
 1               5

<210> SEQ ID NO 7
<211> LENGTH: 7
<212> TYPE: PRT
<213> ORGANISM: Mus musculus

<400> SEQUENCE: 7

Tyr His Gln Pro Asp Asp Lys
 1               5

<210> SEQ ID NO 8
<211> LENGTH: 17
<212> TYPE: DNA
<213> ORGANISM: Artificial Sequence
<220> FEATURE:
<221> NAME/KEY: modified_base
<222> LOCATION: (3)
<223> OTHER INFORMATION: a, g, c or t
<221> NAME/KEY: modified_base
<222> LOCATION: (6)
<223> OTHER INFORMATION: a, g, c or t
<221> NAME/KEY: modified_base
<222> LOCATION: (12)
<223> OTHER INFORMATION: a, g, c or t
<221> NAME/KEY: modified_base
<222> LOCATION: (15)
<223> OTHER INFORMATION: a, g, c or t
<223> OTHER INFORMATION: Description of Artificial Sequence: synthetic
      DNA

<400> SEQUENCE: 8
gtnacngarg gnytnac                                                   17

<210> SEQ ID NO 9
<211> LENGTH: 21
<212> TYPE: DNA
<213> ORGANISM: Artificial Sequence
<220> FEATURE:
<221> NAME/KEY: modified_base
<222> LOCATION: (10)
<223> OTHER INFORMATION: a, g, c or t
<223> OTHER INFORMATION: Description of Artificial Sequence: synthetic
      DNA

<400> SEQUENCE: 9
yttrtcrtcn ggytgrtgrt a                                              21

<210> SEQ ID NO 10
<211> LENGTH: 633
<212> TYPE: PRT
<213> ORGANISM: Unknown Organism
```

```
<220> FEATURE:
<223> OTHER INFORMATION: Description of Unknown Organism: hnRNPR

<400> SEQUENCE: 10

Met Ala Asn Gln Val Asn Gly Asn Ala Val Gln Leu Lys Glu Glu
 1               5                  10                  15

Glu Pro Met Asp Thr Ser Ser Val Thr His Thr Glu His Tyr Lys Thr
                20                  25                  30

Leu Ile Glu Ala Gly Leu Pro Gln Lys Val Ala Glu Arg Leu Asp Glu
            35                  40                  45

Ile Phe Gln Thr Gly Leu Val Ala Tyr Val Asp Leu Asp Glu Arg Ala
        50                  55                  60

Ile Asp Ala Leu Arg Glu Phe Asn Glu Glu Gly Ala Leu Ser Val Leu
65                  70                  75                  80

Gln Gln Phe Lys Glu Ser Asp Leu Ser His Val Gln Asn Lys Ser Ala
                85                  90                  95

Phe Leu Cys Gly Val Met Lys Thr Tyr Arg Gln Arg Glu Lys Gln Gly
            100                 105                 110

Ser Lys Val Gln Glu Ser Thr Lys Gly Pro Asp Glu Ala Lys Ile Lys
        115                 120                 125

Ala Leu Leu Glu Arg Thr Gly Tyr Thr Leu Asp Val Thr Thr Gly Gln
130                 135                 140

Arg Lys Tyr Gly Gly Pro Pro Asp Ser Val Tyr Ser Gly Val Gln
145                 150                 155                 160

Pro Gly Ile Gly Thr Glu Val Phe Val Gly Lys Ile Pro Arg Asp Leu
                165                 170                 175

Tyr Glu Asp Glu Leu Val Pro Leu Phe Glu Lys Ala Gly Pro Ile Trp
            180                 185                 190

Asp Leu Arg Leu Met Met Asp Pro Leu Ser Gly Gln Asn Arg Gly Tyr
        195                 200                 205

Ala Phe Ile Thr Phe Cys Gly Lys Glu Ala Ala Gln Glu Ala Val Lys
        210                 215                 220

Leu Cys Asp Ser Tyr Glu Ile Arg Pro Gly Lys His Leu Gly Val Cys
225                 230                 235                 240

Ile Ser Val Ala Asn Asn Arg Leu Phe Val Gly Ser Ile Pro Lys Asn
                245                 250                 255

Lys Thr Lys Glu Asn Ile Leu Glu Glu Phe Ser Lys Val Thr Glu Gly
            260                 265                 270

Leu Val Asp Val Ile Leu Tyr His Gln Pro Asp Asp Lys Lys Lys Asn
        275                 280                 285

Arg Gly Phe Cys Phe Leu Glu Tyr Glu Asp His Lys Ser Ala Ala Gln
        290                 295                 300

Ala Arg Arg Arg Leu Met Ser Gly Lys Val Lys Val Trp Gly Asn Val
305                 310                 315                 320

Val Thr Val Glu Trp Ala Asp Pro Val Glu Pro Asp Pro Glu Val
                325                 330                 335

Met Ala Lys Val Lys Val Leu Phe Val Arg Asn Leu Ala Thr Thr Val
            340                 345                 350

Thr Glu Glu Ile Leu Glu Lys Ser Phe Ser Glu Phe Gly Lys Leu Glu
        355                 360                 365

Arg Val Lys Lys Leu Lys Asp Tyr Ala Phe Val His Phe Glu Asp Arg
        370                 375                 380

Gly Ala Ala Val Lys Ala Met Asp Glu Met Asn Gly Lys Glu Ile Glu
385                 390                 395                 400
```

```
Gly Glu Glu Ile Glu Ile Val Leu Ala Lys Pro Pro Asp Lys Lys Arg
                405                 410                 415

Lys Glu Arg Gln Ala Ala Arg Gln Ala Ser Arg Ser Thr Ala Tyr Glu
            420                 425                 430

Asp Tyr Tyr His Pro Pro Arg Met Pro Pro Ile Arg Gly
        435                 440                 445

Arg Gly Arg Gly Gly Arg Gly Gly Tyr Gly Tyr Pro Pro Asp Tyr
    450                 455                 460

Tyr Gly Tyr Glu Asp Tyr Tyr Asp Asp Tyr Tyr Gly Tyr Asp Tyr His
465                 470                 475                 480

Asp Tyr Arg Gly Gly Tyr Glu Asp Pro Tyr Tyr Gly Tyr Asp Asp Gly
            485                 490                 495

Tyr Ala Val Arg Gly Arg Gly Gly Arg Gly Arg Gly Ala Pro
                500                 505                 510

Pro Pro Pro Arg Gly Arg Gly Ala Pro Pro Arg Gly Arg Ala Gly
            515                 520                 525

Tyr Ser Gln Arg Gly Ala Pro Leu Gly Pro Arg Gly Ser Arg Gly
    530                 535                 540

Gly Arg Gly Gly Pro Ala Gln Gln Gln Arg Gly Arg Gly Ser Arg Gly
545                 550                 555                 560

Ser Arg Gly Asn Arg Gly Gly Asn Val Gly Gly Lys Arg Lys Ala Asp
                565                 570                 575

Gly Tyr Asn Gln Pro Asp Ser Lys Arg Arg Gln Thr Asn Asn Gln Gln
            580                 585                 590

Asn Trp Gly Ser Gln Pro Ile Ala Gln Gln Pro Leu Gln Gln Gly Gly
        595                 600                 605

Asp Tyr Ser Gly Asn Tyr Gly Tyr Asn Asn Asp Asn Gln Glu Phe Tyr
            610                 615                 620

Gln Asp Thr Tyr Gly Gln Gln Trp Lys
625                 630

<210> SEQ ID NO 11
<211> LENGTH: 335
<212> TYPE: PRT
<213> ORGANISM: Unknown Organism
<220> FEATURE:
<223> OTHER INFORMATION: Description of Unknown Organism: m-hnRNPR

<400> SEQUENCE: 11

Asp His Lys Ser Ala Ala Gln Ala Arg Arg Leu Met Ser Gly Lys
  1               5                  10                  15

Val Lys Val Trp Gly Asn Val Val Thr Val Glu Trp Ala Asp Pro Val
             20                  25                  30

Glu Glu Pro Asp Pro Glu Val Met Ala Lys Val Lys Val Leu Phe Val
         35                  40                  45

Arg Asn Leu Ala Thr Thr Val Thr Glu Glu Ile Leu Glu Lys Ser Phe
     50                  55                  60

Ser Glu Phe Gly Lys Leu Glu Arg Val Lys Lys Leu Lys Asp Tyr Ala
 65                  70                  75                  80

Phe Val His Phe Glu Asp Arg Gly Ala Ala Val Lys Ala Met Asp Glu
                 85                  90                  95

Met Asn Gly Lys Glu Ile Glu Gly Glu Glu Ile Glu Ile Val Leu Ala
            100                 105                 110

Lys Pro Pro Asp Lys Lys Arg Lys Glu Arg Gln Ala Ala Arg Gln Ala
        115                 120                 125
```

-continued

```
Ser Arg Ser Thr Ala Tyr Glu Asp Tyr Tyr His Pro Pro Pro Arg
    130             135             140

Met Pro Pro Pro Met Arg Gly Arg Gly Arg Gly Gly Arg Gly Gly Tyr
145             150             155             160

Gly Tyr Pro Pro Asp Tyr Tyr Gly Tyr Glu Asp Tyr Tyr Asp Asp Tyr
            165             170             175

Tyr Gly Tyr Asp Tyr His Asp Tyr Arg Gly Gly Tyr Glu Asp Pro Tyr
        180             185             190

Tyr Gly Tyr Asp Asp Gly Tyr Ala Val Arg Gly Arg Gly Gly Gly Arg
        195             200             205

Gly Gly Arg Gly Ala Pro Pro Pro Arg Gly Arg Gly Ala Pro Pro
    210             215             220

Pro Arg Gly Arg Ala Gly Tyr Ser Gln Arg Gly Ala Pro Leu Gly Pro
225             230             235             240

Pro Arg Gly Ser Arg Gly Gly Arg Gly Gly Pro Ala Gln Gln Gln Arg
            245             250             255

Gly Arg Gly Ser Arg Gly Ala Arg Gly Asn Arg Gly Gly Asn Val Gly
            260             265             270

Gly Lys Arg Lys Ala Asp Gly Tyr Asn Gln Pro Asp Ser Lys Arg Arg
        275             280             285

Gln Thr Asn Asn Gln Gln Asn Trp Gly Ser Gln Pro Ile Ala Gln Gln
    290             295             300

Pro Leu Gln Gln Gly Gly Asp Tyr Ser Gly Asn Tyr Gly Tyr Asn Asn
305             310             315             320

Asp Asn Gln Glu Phe Tyr Gln Asp Thr Tyr Gly Gln Gln Trp Lys
            325             330             335
```